United States Patent
Stenzler et al.

(10) Patent No.: US 7,955,294 B2
(45) Date of Patent: *Jun. 7, 2011

(54) INTERMITTENT DOSING OF NITRIC OXIDE GAS

(75) Inventors: Alex Stenzler, Long Beach, CA (US); Christopher C. Miller, North Vancouver (CA); Bevin B. McMullin, Surrey (CA)

(73) Assignees: Sensormedics Corporation, Yorba Linda, CA (US); Pulmonox Technologies Corporation, Edmonton, Alberta (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/598,221

(22) Filed: Nov. 10, 2006

(65) Prior Publication Data

US 2007/0144515 A1  Jun. 28, 2007

Related U.S. Application Data

(63) Continuation of application No. PCT/US2005/016427, filed on May 11, 2005.

(60) Provisional application No. 60/570,429, filed on May 11, 2004.

(51) Int. Cl.
*A61M 35/00* (2006.01)
*A61M 16/10* (2006.01)

(52) U.S. Cl. ...... 604/23; 604/290; 604/305; 128/203.12

(58) Field of Classification Search .......... 128/200.14, 128/200.19, 200.24, 203.12, 203.13, 203.14, 128/203.16, 203.18, 203.22, 203.25, 203.29, 128/204.18, 204.21, 204.25, 204.29, 205.11; 604/23; 424/718

See application file for complete search history.

(56) References Cited

U.S. PATENT DOCUMENTS

| 3,036,584 | A | 5/1962 | Lee |
| 3,192,106 | A | 6/1965 | Bracken et al. |
| 4,127,121 | A | 11/1978 | Westenskow et al. |
| 4,191,952 | A | 3/1980 | Schreiber et al. |

(Continued)

FOREIGN PATENT DOCUMENTS

CA    2278053    7/1998

(Continued)

OTHER PUBLICATIONS

Ray, James D. et al., "A New Method of Preparing Nitric Oxide," Contribution from the Department of Chemistry, Stanford University (1956).

(Continued)

*Primary Examiner* — Danton DeMille
(74) *Attorney, Agent, or Firm* — Arent Fox LLP

(57) ABSTRACT

A method and corresponding device are described for combating microbes and infections by delivering intermittent high doses of nitric oxide to a mammal for a period of time and which cycles between high and low concentration of nitric oxide gas. The high concentration of nitric oxide is preferably delivered intermittently for brief periods of time that are interspersed with periods of time with either no nitric oxide delivery or lower concentrations of nitric oxide. The method is advantageous because at higher concentration, nitric oxide gas overwhelms the defense mechanism of pathogens that use the mammalian body to replenish their thiol defense system. A lower dose or concentration of nitric oxide gas delivered in between the bursts of high concentration nitric oxide maintains nitrosative stress pressure on the pathogens and also reduces the risk of toxicity of nitric oxide gas.

21 Claims, 11 Drawing Sheets

U.S. PATENT DOCUMENTS

| | | | |
|---|---|---|---|
| 4,224,941 A | 9/1980 | Stivala | |
| 4,328,823 A | 5/1982 | Schreiber | |
| 4,336,798 A | 6/1982 | Beran | |
| 4,345,612 A | 8/1982 | Koni et al. | |
| 4,442,856 A | 4/1984 | Betz | |
| 4,608,041 A | 8/1986 | Nielsen | |
| 4,611,590 A | 9/1986 | Ryschka et al. | |
| 4,770,168 A | 9/1988 | Rusz et al. | |
| 4,905,685 A * | 3/1990 | Olsson et al. | 128/203.12 |
| 4,954,526 A | 9/1990 | Keefer | |
| 5,154,697 A | 10/1992 | Loori | |
| 5,155,137 A | 10/1992 | Keefer et al. | |
| 5,159,924 A | 11/1992 | Cegielski et al. | |
| 5,197,462 A | 3/1993 | Falb et al. | |
| 5,396,882 A | 3/1995 | Zapol | |
| 5,423,313 A | 6/1995 | Olsson et al. | |
| 5,427,797 A | 6/1995 | Frostell et al. | |
| 5,485,827 A * | 1/1996 | Zapol et al. | 128/200.14 |
| 5,514,204 A | 5/1996 | Sheu et al. | |
| 5,519,020 A | 5/1996 | Smith et al. | |
| 5,531,218 A | 7/1996 | Krebs | |
| 5,536,241 A | 7/1996 | Zapol | |
| 5,558,083 A | 9/1996 | Bathe et al. | |
| 5,570,683 A | 11/1996 | Zapol | |
| 5,615,669 A | 4/1997 | Olsson et al. | |
| 5,632,981 A | 5/1997 | Saavedra et al. | |
| 5,648,101 A | 7/1997 | Tawashi | |
| 5,650,442 A | 7/1997 | Mitchell et al. | |
| 5,651,358 A | 7/1997 | Briend et al. | |
| 5,676,963 A | 10/1997 | Keefer et al. | |
| 5,688,236 A | 11/1997 | Gragg | |
| 5,692,497 A | 12/1997 | Schnitzer et al. | |
| 5,700,830 A | 12/1997 | Korthuis et al. | |
| 5,713,349 A | 2/1998 | Kearney | |
| 5,722,392 A | 3/1998 | Skimming et al. | |
| 5,732,693 A | 3/1998 | Bathe et al. | |
| 5,765,548 A | 6/1998 | Perry | |
| 5,789,447 A | 8/1998 | Wink, Jr. et al. | |
| 5,810,795 A | 9/1998 | Westwood | |
| 5,814,666 A | 9/1998 | Green et al. | |
| 5,814,667 A | 9/1998 | Mitchell et al. | |
| 5,823,180 A | 10/1998 | Zapol | |
| 5,834,030 A | 11/1998 | Bolton | |
| 5,837,736 A | 11/1998 | Mitchell et al. | |
| 5,839,433 A * | 11/1998 | Higenbottam | 128/204.21 |
| 5,840,759 A | 11/1998 | Mitchell et al. | |
| 5,845,633 A | 12/1998 | Psaros | |
| 5,871,009 A * | 2/1999 | Rydgren et al. | 128/203.12 |
| 5,873,359 A | 2/1999 | Zapol et al. | |
| 5,885,621 A | 3/1999 | Head et al. | |
| 5,904,938 A | 5/1999 | Zapol et al. | |
| 5,918,596 A * | 7/1999 | Heinonen | 128/204.21 |
| 5,957,880 A | 9/1999 | Igo et al. | |
| 6,000,403 A | 12/1999 | Cantwell | |
| 6,019,100 A | 2/2000 | Alving et al. | |
| 6,060,020 A | 5/2000 | Piuk et al. | |
| 6,063,407 A | 5/2000 | Zapol et al. | |
| 6,067,983 A | 5/2000 | Stenzler | |
| 6,071,254 A | 6/2000 | Augustine | |
| 6,073,627 A | 6/2000 | Sunnen | |
| 6,083,209 A | 7/2000 | Marasco, Jr. | |
| 6,089,229 A | 7/2000 | Bathe et al. | |
| 6,103,275 A | 8/2000 | Seitz et al. | |
| 6,109,260 A | 8/2000 | Bathe | |
| 6,110,895 A | 8/2000 | Rodgers et al. | |
| 6,125,846 A | 10/2000 | Bathe et al. | |
| 6,131,572 A | 10/2000 | Heinonen | |
| 6,142,147 A * | 11/2000 | Head et al. | 128/204.21 |
| 6,158,434 A | 12/2000 | Lugtigheid et al. | |
| 6,160,021 A | 12/2000 | Lerner et al. | |
| 6,164,276 A | 12/2000 | Bathe et al. | |
| 6,190,704 B1 | 2/2001 | Murrell | |
| 6,200,558 B1 | 3/2001 | Saavedra et al. | |
| 6,232,336 B1 | 5/2001 | Hrabie et al. | |
| 6,270,779 B1 | 8/2001 | Fitzhugh et al. | |
| 6,358,536 B1 | 3/2002 | Thomas | |
| 6,379,660 B1 | 4/2002 | Saavedra et al. | |
| 6,432,077 B1 * | 8/2002 | Stenzler | 604/23 |
| 6,472,390 B1 | 10/2002 | Stamler et al. | |
| 6,494,314 B1 | 12/2002 | Lamborne et al. | |
| 6,511,991 B2 | 1/2003 | Hrabie et al. | |
| 6,555,058 B2 | 4/2003 | Kamibayashi et al. | |
| 6,571,790 B1 | 6/2003 | Weinstein | |
| 6,581,599 B1 * | 6/2003 | Stenzler | 128/204.23 |
| 6,601,580 B1 | 8/2003 | Block et al. | |
| 6,668,828 B1 * | 12/2003 | Figley et al. | 128/204.18 |
| 6,673,338 B1 | 1/2004 | Arnold et al. | |
| 6,703,046 B2 | 3/2004 | Fitzhugh et al. | |
| 6,706,274 B2 | 3/2004 | Herrmann et al. | |
| 6,715,485 B1 | 4/2004 | Djupesland | |
| 6,747,062 B2 | 6/2004 | Murrell | |
| 6,750,254 B2 | 6/2004 | Hrabie et al. | |
| 6,758,214 B2 | 7/2004 | Fine et al. | |
| 6,780,849 B2 | 8/2004 | Herrmann et al. | |
| 6,786,217 B2 | 9/2004 | Stenzler | |
| 6,793,644 B2 | 9/2004 | Stenzler | |
| 6,796,966 B2 | 9/2004 | Thomas | |
| 6,811,965 B2 | 11/2004 | Vodovotz et al. | |
| 6,867,194 B2 | 3/2005 | Wang et al. | |
| 6,887,485 B2 | 5/2005 | Fitzhugh et al. | |
| 6,911,478 B2 | 6/2005 | Hrabie et al. | |
| 6,920,876 B2 | 7/2005 | Miller et al. | |
| 6,935,334 B2 * | 8/2005 | Bloch et al. | 128/200.14 |
| 6,938,357 B2 | 9/2005 | Hauch | |
| 6,949,530 B2 | 9/2005 | Hrabie et al. | |
| 7,025,869 B2 * | 4/2006 | Fine et al. | 205/553 |
| 7,040,313 B2 * | 5/2006 | Fine et al. | 128/203.12 |
| 7,048,951 B1 | 5/2006 | Seitz et al. | |
| 7,105,502 B2 | 9/2006 | Arnold et al. | |
| 7,118,767 B2 | 10/2006 | Kim et al. | |
| 7,122,018 B2 | 10/2006 | Stenzler et al. | |
| 7,199,154 B2 | 4/2007 | Berthelette et al. | |
| 7,201,166 B2 * | 4/2007 | Blaise et al. | 128/203.12 |
| 2002/0069877 A1 | 6/2002 | Villareal | |
| 2002/0082566 A1 | 6/2002 | Stenzler | |
| 2002/0119115 A1 | 8/2002 | Keefer et al. | |
| 2002/0138051 A1 * | 9/2002 | Hole et al. | 604/305 |
| 2002/0155164 A1 | 10/2002 | Figley et al. | |
| 2002/0156416 A1 | 10/2002 | Stenzler | |
| 2002/0169202 A1 | 11/2002 | Sakamoto et al. | |
| 2002/0185126 A1 * | 12/2002 | Krebs | 128/200.24 |
| 2003/0039697 A1 | 2/2003 | Zhao et al. | |
| 2003/0150457 A1 | 8/2003 | Miller et al. | |
| 2003/0165578 A1 | 9/2003 | Murrell | |
| 2003/0172929 A1 | 9/2003 | Muellner | |
| 2003/0203915 A1 | 10/2003 | Fang et al. | |
| 2003/0215528 A1 | 11/2003 | Graham et al. | |
| 2003/0228564 A1 | 12/2003 | Edrich et al. | |
| 2004/0009238 A1 | 1/2004 | Miller et al. | |
| 2004/0043026 A1 | 3/2004 | Tuan et al. | |
| 2004/0081580 A1 | 4/2004 | Hole et al. | |
| 2004/0112378 A1 | 6/2004 | Djupesland | |
| 2004/0131703 A1 | 7/2004 | Bach et al. | |
| 2004/0163647 A1 | 8/2004 | Figley et al. | |
| 2004/0180863 A1 | 9/2004 | Hrabie et al. | |
| 2004/0259840 A1 | 12/2004 | Herrmann et al. | |
| 2005/0016427 A1 | 1/2005 | Memory | |
| 2005/0079148 A1 | 4/2005 | Fitzhugh et al. | |
| 2005/0137521 A1 | 6/2005 | Stenzler | |
| 2005/0142217 A1 | 6/2005 | Adams et al. | |
| 2005/0148566 A1 | 7/2005 | Waterhouse et al. | |
| 2005/0171066 A1 | 8/2005 | Shami | |
| 2005/0191372 A1 | 9/2005 | Stenzler et al. | |
| 2005/0217668 A1 | 10/2005 | Figley et al. | |
| 2005/0217679 A1 | 10/2005 | Miller et al. | |
| 2005/0251117 A1 | 11/2005 | Anderson et al. | |
| 2005/0265958 A1 | 12/2005 | West et al. | |
| 2005/0288260 A1 | 12/2005 | Hrabie et al. | |
| 2006/0008529 A1 | 1/2006 | Meyerhoff et al. | |
| 2006/0068031 A1 | 3/2006 | Miller et al. | |
| 2006/0147553 A1 | 7/2006 | Miller et al. | |
| 2007/0065473 A1 | 3/2007 | Miller et al. | |
| 2007/0086954 A1 | 4/2007 | Miller et al. | |
| 2007/0088316 A1 | 4/2007 | Stenzler et al. | |
| 2007/0104653 A1 | 5/2007 | Miller et al. | |

FOREIGN PATENT DOCUMENTS

| | | |
|---|---|---|
| CA | 2350883 | 6/2000 |
| DE | 197 01 617 A1 | 7/1998 |
| DE | 003713396 A1 | 11/1998 |
| EP | 0640356 A1 | 3/1995 |
| EP | 0640357 A1 | 3/1995 |
| EP | 0 659 445 A1 | 6/1995 |
| EP | 0659445 A1 | 6/1995 |
| EP | 0659445 B1 | 6/1995 |
| EP | 1243278 A2 | 9/2002 |
| FR | 2656218 | 6/1991 |
| JP | 3-139364 | 6/1991 |
| JP | 3-207365 | 9/1991 |
| KR | 202066 | 6/1999 |
| WO | WO 92/17445 | 10/1992 |
| WO | WO 93/15779 | 8/1993 |
| WO | WO 93/17741 | 9/1993 |
| WO | WO 95/09612 | 4/1995 |
| WO | WO 95/10173 A2 | 4/1995 |
| WO | WO 95/26768 | 10/1995 |
| WO | WO 96/00006 | 1/1996 |
| WO | WO 96/22803 | 8/1996 |
| WO | WO 96/25184 | 8/1996 |
| WO | WO 96/31217 | 10/1996 |
| WO | WO 98/01142 | 1/1998 |
| WO | WO 98/44976 A1 | 10/1998 |
| WO | WO 99/49921 | 10/1999 |
| WO | WO 00/07653 | 2/2000 |
| WO | WO 00/30659 | 6/2000 |
| WO | WO 01/65935 A1 | 9/2001 |
| WO | WO 02/056864 A2 | 7/2002 |
| WO | WO 03/066109 A1 | 8/2003 |
| WO | WO 2005/060603 A3 | 7/2005 |
| WO | WO 2005/110052 A3 | 11/2005 |
| WO | WO 2005/110441 A2 | 11/2005 |
| WO | WO 2006/110923 | 10/2006 |

OTHER PUBLICATIONS

Shank, J. L. et al., "The Effect of Nitric Oxide on Bacteria," Applied Microbio, No. 10, 189-189 (1962).
Norman, C. et al., "Nitrogen Oxides in Tobacco Smoke," Nature, vol. 205, No. 4971, pp. 915-916, (Feb. 1965).
Canetti, G., "Present aspects of bacterial resistance in tuberculosis," Am. Rev. Respir. Dis. 92:687-703 (1965).
Bass, H. et al., "Regional structure and function in brochiectasis," Am. Rev. Respir. Dis. 97:598-609 (1968).
Contractor, A. M. et al., "Development and Evaluation of an Inhalation Aerosol of Nitroglycerin," Journal of Pharmaceutical Sciences, vol. 63, No. 6, pp. 907-911 (Jun. 1974).
Oda, H. et al., "Nitrosyl-Hemoglobin Formation in the Blood of Animals Exposed to Nitric Oxide," Archives of Environmental Health, vol. 30, No. 7, pp. 453-456 (Sep. 1975).
Katsuki, S. et al., "Stimulation of Guanylate Cyclase by Sodium Nitroprusside, Nitroglycerin and Nitric Oxide in Various Tissue Preparations and Comparison to the Effects of Sodium Azide and Hydroxylamine." Journal of Cyclic Nucleotide Research. vol. 3. pp. 23-25 (1977).
Hugod, C., "Effect of exposure of 43 PPM nitric oxide and 3.6 PPM nitrogen dioxide on rabbit lung," Arch. Occup. Environ. Health 42:159-167 (1979).
Yoshida, J. et al., "Metabolic Fate of Nitric Oxide," Int Arch Occup Environ Health, vol. 46, No. 1, pp. 71-77 (Apr. 1980).
Borland, C., "The Fate of Inhaled Nitric Oxide," Clinical Science, Abstract No. 104, p. 37P (1983).
Mancinelli et al., "Effects of Nitric Oxide and Nitrogen Dioxide on Bacterial Growth," Applied and Environmental Microbiology, vol. 46, No. 1, pp. 198-202 (Jul. 1983).
Demling, R. H. et al., "The Pulmonary and Systemic Response to Recurrent Endotoxemia in the Adult Sheep," Surgery, vol. 100, No. 5, pp. 876-883 (Nov. 1986).
Higenbottam, T., "Primary Pulmonary Hypertension," British Medical Journal, vol. 293, pp. 1456-1457 (Dec. 1986).
Higenbottam, T. et al., "Primary Pulmonary Hypertension," British Medical Journal, vol. 294, p. 705 (Mar. 1987).
Palmer, R.M.J. et al., "Nitric Oxide Release Accounts for the Biological Activity of Endothelium-Derived Relaxing Factor," Nature, vol. 327, pp. 524-526 (Jun. 1987).
Ignarro, L. J. et al., "Endothelium-Derived Relaxing Factor Produced and Released From Artery and Vein is Nitric Oxide," Proceedings of the National Academy of Sciences of the United States of America. vol. 84, No. 24, No. 9265-9269 (Dec. 1987).
Higenbottam, T. W. et al., "Inhaled 'Endothelium Derived-Relaxing Factor' (EDRF) in Primary Hypertension (PPH)," Abstract, American Review of Respiratory Disease, Suppl., vol. 137, No. 4, Part 2, p. 107 (Apr. 1988).
Ignarro, L. J. et al., "Endothelium-Derived Relaxing Factor and Nitric Oxide Possess Identical Pharmacologic Properties as Relaxants of Bovine Arterial and Venous Smooth Muscle." The Journal of Pharmacology and Experimental Therapeutics, vol. 246, No. 1, pp. Dinh-Xuan, A. T. et al., "Non-Prostanoid Endothelium-Derived Vasoactive Factors," The Journal of International Medical Research, vol. 17, pp. 305-315 (1989).
Borland, C. D. R. et al., "A Simultaneous Single Breath Measurement of Pulmonary Diffusing Capacity with Nitric Oxide and Carbon Monoxide," The European Respiratory Journal, vol. 2, No. 1, pp. 56-63 (Jan. 1989).
Buga, G. M. et al., "Endothelium-Derived Nitric Oxide Relaxes Nonvascular Smooth Muscle," European Journal of Pharmacology, vol. 161, No. 1, pp. 61-72, (Feb. 1989).
Garg, U. C. et al., "Nitric Oxide-generating Vasodilators and 8-Bromo-Cyclic Guanosine Monophosphate Inhibit Mitogensis and Proliferation of Cultured Rat Vascular Smooth Muscle Cells," The Journal of Clinical Investigation, vol. 83, No. 5, pp. 1774-1777 (May 1989).
Meyer, M. et al., "Nitric Oxide (NO), a New Test Gas for Study of Alveolar-capillary Diffusion," The European Respiratory Journal, vol. 2, No. 6, pp. 494-496 (Jun. 1989).
Dinh-Xuan, A. T. et al., "Primary Pulmonary Hypertension: Diagnosis, Medical and Surgical Treatment," vol. 84, pp. 189-197 (1990).
Stavert, D. M. et al., "Nitric Oxide and Nitrogen Dioxide as Inducers of Acute Pulmonary Injury When Inhaled at Relatively High Concentrations for Brief Periods," Inhalation Toxicology 2:53-67 (1990).
Moinard, J. et al., "Determination of Lung Capillary Blood Volume and Membrane Diffusing capacity in Patients with COLD using the NO-CO Method," The European Respiratory Journal, vol. 3, pp. 318-322 (1990).
Archer, S. L., "Comparison of the Hemodynamic Effects of Nitric Oxide and Endothelium-Dependent Vasodilators in Intact Lungs," Journal of Applied Physiology, vol. 68, No. 2, pp. 735-747 (Feb. 1990).
Meyer, M. et al., "Pulmonary Diffusing Capacities for Nitric Oxide and carbon Monoxide Determined by Rebreathing in Dogs," Journal of Applied Physiology, vol. 68, No. 6, pp. 2344-2357 (Jun. 1990).
Vane, J. R. et al., "Regulatory Functions of the Vascular Endothelium," The New England Journal of Medicine, vol. 323, No. 1, pp. 27-36 (Jul. 1990).
Higenbottam, T. et al., "Has the Treatment of Asthma Improved?" Chest, vol. 98, No. 3, pp. 706-712 (Sep. 1990).
Swami, A. et al., "The Pulmonary Physician and critical Care: 2. The Injury Lung: Conventional and Novel Respiratory Therapy," Thorax, vol. 47, pp. 555-562 (1992).
Bult, H. et al., "Chronic Exposure to Exogenous Nitric Oxide May Suppress its Endogenous Release and Efficacy," Journal of Cardiovascular Pharmacology, vol. 17, Suppl. 3, pp. S79-S82 (1991).
Frostell, C. et al., "Inhaled Nitric Oxide, A Selective Pulmonary Vasodilator Reversing Hypoxic Pulmonary Vasoconstriction," Circulation Journal of the American Heart Association, vol. 83, pp. 2083-2047 (1991).
Hendrickson, D.A. et al, "Regents and Stains," Manual of Clinical Microbiology, 5th Ed., American Society for Microbiology, pp. 1289-1314 (1991).
Cremona, g. et al., "Endothelium-derived Relaxing Factor and the Pulmonary Circulation," Lung, vol. 169, pp. 185-202 (1991).
Falke, K. et al., "Inhaled Nitric Oxide Selectively Reduces Pulmonary Hypertension in Severe ARDS and Improves Gas Exchange as well as right Heart Ejection fraction—A Case Report," Abstract 248, Am. Rev. Respir. Dis., vol. 143 (1991).

Fratacci, M. D., "Inhaled Nitric Oxide—A Selective Pulmonary Vasodilator of Heparin-Protamine Vasoconstriction in Sheep," Anesthesiology, vol. 75, pp. 990-999 (1991).
Denis, M., "Interferon—Gamma-treated Murine Macrophages Inhibit Growth of Tubercle Bacilli via the Generation of Reactive Nitrogen Intermediates," Cellular Immunology, vol. 132. No. 1, pp. 150-157 (Jan. 1991).
Dinh-Xuan, A. T. et al., "Impairment of Endothelium-Dependent Pulmonary-Artery Relaxation in Chronic Obstructive Lung Disease," The New England Journal of Medicine, vol. 324, No. 22, pp. 1539-1547 (May 1991).
Frostell, C. et al., "Inhaled Nitric Oxide—A Selective Pulmonary Vasodilator Reversing Hypoxic Pulmonary Vasoconstriction," Circulation, vol. 83, No. 6 (Jun. 1991).
Moncada, S. et al., "Nitric Oxide: Physiology, Pathophysiology, and Pharmacology," Pharmacological Reviews, vol. 43, No. 2 (Jun. 1991).
Frostell, C. et al., "Inhaled Nitric Oxide Dilates Human Hypoxic Pulmonary Vasoconstriction Without Causing Systemic Vasodilation," Anesthesiology, The Journal of The American Society of Anesthesiologists, Inc., vol. 75, No. 3A, Abstract A989 (Sep. 1991).
Girard, C. et al., "Inhaled Nitric Oxide (NO) in Pulmonary Hypertension Following Mitral Valve Replacement," Anesthesiology, The Journal of The American Society of Anesthesiologists, Inc., vol. 75, No. 3A, Abstract A983 (Sep. 1991).
Roberts, J. D. et al., "Inhaled Nitric Oxide (NO): A Selective Pulmonary Vasodilator for the Treatment of Persistent Pulmonary Hypertension of the Newborn (PPHN)," Abstract 1279, Circulation, vol. 84. No. 4, p. II-321 (Oct. 1991).
Pepke-Zaba, J. et al., "Inhaled Nitric Oxide as a Cause of Selective Pulmonary Vasodilatation in Pulmonary Hypertension," The Lancet, vol. 338, No. 8776, pp. 1173-1174 (Nov. 1991).
Radomski, M. W., et al., "Human Colorectal Adenocarcinoma Cells: Differential Nitric Oxide Synthesis Determines Their Ability to Aggregate Platelets," Cancer Research, vol. 51, pp. 6073-6078 (Nov. 15. 1991).
Johns, R. A., "EDRF/Nitric Oxide—The Endogenous Nitrovasodilator and a New cellular Messenger," Anesthesiology, The Journal of the American Society of Anesthesiologists, Inc., vol. 75, No. 6, pp. 927-931 (Dec. 1991).
Pearl, R. G., "The Pulmonary Circulation," Anesthesiology, vol. 5, pp. 848-854 (1992).
Chan, J. et al., "Killing of Virulent Mycobacterium Tuberculosis by Reactive Nitrogen Intermediates Produced by Activated Murine Macophages," J. Exp. Med. 175:1111-1122 (Apr. 1992).
Rossiant, R. et al., "Successful Treatment of Severe Adult Respiratory Distress Syndrome with Inhaled Nitric Oxide," American Review of Respiratory Disease, Suppl., vol. 145, No. 4, Part 2, p. A80 (Apr. 1992).
Rossiant, R. et al., "Inhaled Nitric Oxide in Contrast to Infused Prostacyclin Selectively Reduces Pulmonary Hypertension and Improves Gas Exchange in Severe ARDS," Abstract, American Review of Respiratory Disease, Suppl., vol. 145, No. 4, Part 2, p. A185, 1997.
Bigatello, L. M., "Inhaled Nitric Oxide is a Selective Pulmonary Vasodilator in Septic Patients with Severe ARDS," Abstract, American Review of Respiratory Disease, Suppl., vol. 145, No. 4, Part 2, p. A185 (Apr. 1992).
Snyder, S. H. et al., Biological Roles of Nitric Oxide, Scientific American, vol. 266, No. 5, pp. 68-77 (May 1992).
Foubert, L., "Safety Guidelines for Use of Nitric Oxide," The Lancet, vol. 339, No. 8809, pp. 1615-1616 (Jun. 1992).
Messent, M. et al., "Pharmacotherapy in Lung Injury," Thorax, vol. 47, No. 7, pp. 651-656 (Jul. 1992).
Barash, P. et al., "Anesthesiology," The Journal of the American Medical Association, vol. 268, No. 3, pp. 335-337 (Jul. 1992).
Dupuy, P. M. et al., "Bronchodilator Action of Inhaled Nitric Oxide in Guinea Pigs," J. Clin. Invest., vol. 90, pp. 421-428 (Aug. 1992).
Kinsella, J. P. et al., "Hemodynamic Effects of Exogenous Nitric Oxide in Ovine Transitional Pulmonary Circulation," American Journal of Physiology: Heart and Circulatory Physiology, vol. 32, No. 3, pp. H875-H880 (Sep. 1992).
Roberts, J. D. et al., "Inhaled Nitric Oxide in Persistent Pulmonary Hypertension of the Newborn," The Lancet, vol. 340, pp. 818-819 (Oct. 1992).
Kinsella, J. P. et al., "Low-Dose Inhalational Nitric Oxide in Persistent Pulmonary Hypertension of the Newborn," The Lancet, vol. 340, pp. 819-820 (Oct. 1992).
Girard, C. et al., "Inhaled Nitric Oxide After Mitral Valve Replacement in Patients with Chronic Pulmonary Artery Hypertension," Anesthesiology, The Journal of the American Society of Anesthesiologists, Inc., vol. 77, No. 5, pp. 880-883 (Nov. 1992).
Kacmarek, R. M., "Nitric Oxide as a Bronchodilator in Methacholine Induced Bronchospasm in Mild Asthmatics," Abstract (1993).
Blomqvist, H. et al., "Enhanced Pneumonia Resolution by Inhalation of Nitric Oxide?" Acta Anaesthesiol Scand, vol. 37, pp. 110-114 (1993).
Buga, G. M. et al., "Negative Feedback Regulation of Endothelial Cell Function by Nitric Oxide," Circulation Research, Journal of the American Heart Association, 73:808-812 (1993).
Higenbottam, T., "Inhaled Nitric Oxide: A Magic Bullet?" Quarterly Journal of Medicine, vol. 86, pp. 555-558 (1993).
Stenqvist, O. et al., "Evaluation of a New System for Ventilatory Administration of Nitric Oxide," Acta Anaesthesiologica Scandinavica, pp. 687-691 (1993).
Rossaint, R. et al., "Inhaled Nitric Oxide for The Adult Respiratory Distress Syndrome," New England Journal of Medicine, vol. 328, pp. 399-405 (Feb. 1993).
Maragos, C. M., et al., "Nitric Oxide/Nucleophile Complexes Inhibit the in Vitro Proliferation of A375 Melanoma Cells via Nitric Oxide Release," Cancer Release, vol. 53, pp. 564-568 (Feb. 1, 1993).
Pearl, R. G., "Inhaled Nitric Oxide—The Past, The Present and the Future," Anesthesiology, vol. 78, No. 3, pp. 413-416 (Mar. 1993).
Assreuy, J. et al., "Feedback Inhibition of Nitric Oxide Synthase Activity by Nitric Oxide," British Journal of Pharmacology, vol. 108, pp. 883-837 (Mar. 1993).
Higenbottam, T. et al., "Highlights on Pulmonary Hypertension: A Commentary," The European Respiratory Journal, vol. 6, No. 7, pp. 932-933 (Jul. 1993).
Haworth, S. G., "Pulmonary Hypertension in Childhood," The European Respiratory Journal, vol. 6, No. 7, pp. 1037-1043 (Jul. 1993).
Higenbottam, T. et al., "Acute and Chronic Hypoxic Pulmonary Hypertension," The European Respiratory Journal, vol. 6, No. 8, pp. 1207-1212 (Sep. 1993).
Mansch, R. et al., "Simulation of Microbiologically and chemically Influenced corrosion of Natural Sandstone," Abstract, ASTM Special Technical Publication, 203-16; 1 pg. (1994).
Lowenstein, C. J. et al., "Nitric Oxide: a Physiologic Messenger," Annals of Internal Medicine, vol. 120, Issue 3, pp. 227-237 (Feb. 1994).
Dong, Z., et al., "Inverse Correlation Between Expression of Inducible Nitric Oxide Synthase Activity and Production of Metastasis in K-1735 Murine Melanoma Cells," Cancer Research, vol. 54, pp. 789-793 (Feb. 1, 1994).
Butt, A. Y. et al., "New Therapies for Primary Pulmonary Hypertension," Chest, vol. 105, No. 2, pp. 21S-25S (Feb. 1994).
Foubert, L. et al., "Nitric Oxide in Pulmonary Hypertension: Therapeutic Considerations," Journal of Cardiothoracic and Vascular Anesthesia, vol. 8, No. 3, Suppl. 2, p. 41 (Jun. 1994).
Snow, D. et al., "Inhaled Nitric Oxide in Pulmonary Hypertension," Journal of Cardiothoracic and Vascular Anesthesia, vol. 8, No. 3, Suppl. 2, Abstract No. 127 (Jun. 1994).
O'Brien, L. et al., Strains of Mycobacterium Tuberculosis Differ in Susceptibility to Reactive Nitrogen Intermediates in Vitro, Infection and Immunity, vol. 62, No. 11, pp. 5187-5190 (Aug. 1994).
Young, J. D., "A Universal Nitric Oxide Delivery System," British Journal of Anaesthesia, vol. 73, No. 4, pp. 700-702 (Oct. 1994).
Hanson, S. R., et al., "Nitric Oxide Donors: A Continuing Opportunity in Drug Design," Nitric Oxide Biochemistry, Molecular Biology, and Therapeutic Implications, Advances in Pharmacology, vol. 34, pp. 383-398 (1995).
Chan, J. et al., "Effects of Nitric Oxide Synthase Inhibitors on Murine Infection with Mycobacterium Tuberculosis," Infection and Immunity, vol. 63, No. 2., pp. 736-740 (Feb. 1995).

DeGroote, M. A., et al., "NO Inhibitions: Antimicrobial Properties of Nitric Oxide," Clinical Infectious Diseases, vol. 21, Suppl. 2, pp. S162-S165 (Oct. 1995).

Body, S. C., M.D. et al., "Nitric Oxide: Delivery, Measurement, and Clinical Application," Journal of Cardiothoracic and Vascular Anesthesia, vol. 9, No. 6, pp. 748-763 (Dec. 1995).

Higenbottam, T. et al., "The Treatment of Primary Pulmonary Hypertension," Therapeutic Applications of Iloprost, A Volume in the Clinical Monograph Series, pp. 35-41 (Apr. 1995).

Szabo, C., "The Pathophysiological Role of Peroxynitrite in Shock, Inflammation and Ischemia-Reperfusion Injury," Shock, vol. 6, No. 2, pp. 79-88 (1996).

Higenbottam, T., "Nitric Oxide and the Lung," Horizons in Medicine, No. 7 pp. 203-224 (1996).

Young, J. D. et al., "Delivery and Monitoring of Inhaled Nitric Oxide," Intensive Care Medicine, vol. 22, No. 1, pp. 77-86 (Jan. 1996).

Mellgren, K., et al., "Nitric Oxide in the Oxygenator Sweep Gas Reduces Platelet Activation During Experimental Perfusion," The Annals of Thoracic Surgery, vol. 61, No. 4, pp. 1194-1198 (Apr. 1996).

Ramnarine, S. I., et al., "Nitric Oxide Inhibition of Basal and Neurogenic Mucus Secretion in Feerrete Trachea in Vitro," British Journal of Pharmacology, vol. 118 (4), pp. 998-1002 (Jun. 1996).

Channick, R. N., M.D. et al., "Pulsed Delivery of Inhaled Nitric Oxide to Patients with Primary Pulmonary Hypertension," Chest, The Cardiopulmonary and Critical Care Journal, vol. 109, No. 6, pp. 1545-1549 (Jun. 1996).

Hudome, S. M., M.D. et al., "Precise Control of Nitric Oxide Concentration in the Inspired Gas of Continuous Flow Respiratory Devices," Pediatric Pulmonology, vol. 22, No. 3, pp. 182-187 (Sep. 1996).

Cuthbertson, B. H. et al., "Inhaled Nitric Oxide," The Lancet, vol. 348, No. 9039, pp. 1447-1448 (Nov. 1996).

Gerlach, H. et al., "Low Levels of Inhaled Nitric Oxide in Acute Lung Injury," Nitric Oxide and the Lung, vol. 98, Chapter 14, pp. 271-283 (1997).

Dupuy, P. M. et al., "Bronchial Effects of Nitric Oxide," Nitric Oxide and the Lung, vol. 98, Chapter 15, pp. 285-311 (1997).

Leopold, J. A. et al., "New Developments in Nitrosovasodilator Therapy," Vascular Medicine, vol. 2, No. 3 (1997).

Rook, G. A. W., "Intractable Mycobacterial Infections Associated with Genetic Defects in the Receptor for Interferon Gamma: What Does This Tell Us About Immunity to Mycobacteria?" Thorax, vol. 52 (Suppl. 3), pp. S41-S46 (1997).

Katayama, Y. et al., "Inhaled Nitric Oxide and Arterial Oxygen Tension in Patients with chronic Obstructive Pulmonary Disease and Severe Pulmonary Hypertension," Thorax, The Journal of the British Thoracic Society, vol. 52, pp. 120-124 (1997).

Neonatal Inhaled Nitric Oxide Study Group, "Inhaled Nitric Oxide in Full-Term and Nearly Full-Term Infants with Hypoxic Respiratory Failure," New England Journal of Medicine, 336(9):597-604 (Feb. 1997).

Roberts, J. D. et al., "Inhaled Nitric Oxide and Persistent Pulmonary Hypertension of the Newborn," New England Journal of Medicine, 336:605-610 (Feb. 1997).

Imanaka, H., M.D. et al., "Inaccuracies of Nitric Oxide Delivery Systems During Adult Mechanical Ventilation," Anesthesiology, vol. 86, No. 3, pp. 676-688 (Mar. 1997).

Marriott, H. et al., "The Role of Nitric Oxide in Respiratory Disease," Schweiz Med Wochenschr, vol. 127, pp. 709-714 (Apr. 1997).

Nozaki, Y. et al., "Mechanism of Nitric Oxide-Dependent Killing of Mycobacterium bovis BCG in Human Alveolar Macrophages," Infection and Immunity, vol. 65, pp. 3644-3647 (Sep. 1997).

Hess, D., RRT, Ph.D. et al., "Delivery Systems for Inhaled Nitric Oxide," Respiratory Care Clinics of North America, vol. 3, No. 3, pp. 371-410 (Sep. 1997).

Hoehn T., M.D. et al., "Effect of Therapeutic Concentrations of Nitric Oxide on Bacterial Grown in Vitro," Crit Care Med, vol. 26, No. 11, pp. 1857-1862 (1998).

Bauer, J. A. et al., Evaluation of Linear Polyethylenei-mine/Nitric Oxide Adduct on Wound Repair: Therapy Versus Toxicity, The Wound Healing Society, pp. 569-577 (1998).

Pizzichini, M. M. M. et al., "Asthma and Natural Colds: Inflammatory Indices in Induced Sputum: A Feasibility Study," American Journal of Respiratory Critical Care Medicine, vol. 158, pp. 1178-1184 (1998).

Higenbottam, T. et al., "Primary and Secondary Pulmonary Hypertension," Seminars in Respiratory and Critical Care Medicine, vol. 19, No. 1, pp. 91-95 (1998).

Long R. et al., "Pulmonary Tuberculosis Treated with Directly Observed Therapy: Serial Changes in Lung Structure and Function," Chest, vol. 113, pp. 933-943 (1998).

Klein, M.D. et al., "Nitric Oxide Delivery Systems," Acta Anaesthesiologica Scandinavica, pp. 274-275 (1998).

Francoe, M, RRT et al., "Inhaled Nitric Oxide: Technical Aspects of Administration and Monitoring," Critical Care Medicine, vol. 26, No. 4, pp. 782-796 (Apr. 1998).

Keefer, L. K., "Nitric Oxide-Releasing Compounds: From Basic Research to Promising Drugs," The American Chemical Society, vol. 28, pp. 30-35 (Aug. 1998).

Ivy, D. D., M.D. et al., "Acute Hemodynamic Effects of Pulsed Delivery of Low Flow Nasal Nitric Oxide in Children with Pulmonary Hypertension," The Journal of Pediatrics, vol. 133, No. 3, pp. 453-456 (Sep. 1998).

Hiesmayr, M. J. et al., "Performance of Proportional and Continuous Nitric Oxide Delivery Systems During Pressure- and Volume-Controlled Ventilation," The British Journal of Anaesthesia, vol. 81, No. 4, pp. 544-552 (Oct. 1998).

Katayama, Y., M.D. et al., "Minimizing the Inhaled Dose of NO With Breath-by-Breath Delivery of Spikes of Concentrated Gas," Circulation, Journal of the American Heart Association, vol. 98, No. 22 (Dec. 1998).

Higenbottam, T. et al., "Treatments for Severe Pulmonary Hypertension," The Lancet, vol. 353, No. 9150, pp. 338-340 (Jan. 1999).

Long, R. et al., "Mycobacteriocidal Action of Exogenous Nitric Oxide," Antimicrobial Agents and Chemotherapy, vol. 43, No. 2, pp. 403-405, (Feb. 1999).

Schofnagl, H. et al., "Proportional and Continuous NO Delivery Systems," British Journal of Anaesthesia, vol. 82, No. 4, pp. 647-653 (Apr. 1999).

Rimmelzwaan, G. F. et al., "Inhibition of Influenza Virus Replication by Nitric Oxide," Journal of Virology, American Society for Microbiology, vol. 73, No. 10, pp. 8880-8883 (Oct. 1999).

Webert, K. E., M.D. et al., "Effects of Inhaled Nitric Oxide in a Rat Model of *Pseudomonas ceruginosa* Pneumonia," Crit Car Med, vol. 28, No. 7, pp. 2397-2405 (2000).

Tamaoki, J., M.D., et al., "Impairment of Airway Mucociliary Transport in Patients with Sinobronchial Syndrome: Role of Nitric Oxide," Journal of Aerosol Medicine, vol. 13, No. 3, pp. 239-244 (Nov. 2000).

Long et al., "Treatment of Sputum-Smear Positive Pulmonary Tuberculosis With Inhaled Nitric Oxide," 2001-Abstract Form to the ATS 2001 San Francisco, May 18-23, 2001 (faxed Mar. 27, 2001).

Frank, S., et al., "Nitric Oxide Drives Skin Repair: Novel Functions of an Established Mediator," Kidney International, vol. 61, pp. 882-888 (2002).

Imada, M., et al., "Functional Roles of Nasal Nitric Oxide in Nasal Patency and Mucociliary Function," ACTA Oto-Laryngologica, vol. 122, No. 5, pp. 513-519 (Jul. 2002).

Kirov, M. Y., M.D., et al., "Combination of Intravenously Infused Methylene Blue and Inhaled Nitric Oxide Ameliorates Endotoxin-Induced Lung Injury in Awake Sheep," Critical Care Medicine, vol. 31, No. 1, pp. 179-186 (Jan. 2003).

Shami, P. J., et al., JS-K, A Glutathione/Glutathione S-Transferase-activated Nitric Oxide Donor of the Diazeniumdiolate Class with Potent Antineoplastic Activity, Molecular Cancer Therapeutics, vol. 2, pp. 409-417 (Apr. 2003).

Counter-Defendant's First Amended Responses to Counterclaimant's Second Set of Interrogatories Relating to Counterclaims (Nos. 19-38) (Oct. 2003).

Miller, Chris C. et al.; "Treatment of Chronic Nonhealing Leg Ulceration with Gaseous Nitric Oxide: A Case Study"; Journal of Cutaneous Medicine and Surgery, pp. 233-238 (2004).

Vijh, A. K., "High Infectious Burden, Low Cancer Incidence, and Early Malignancy in Developing Countries: A Molecular Hypothesis in Term of the Role of Nitric Oxide," Medical Hypotheses, vol. 63, pp. 208-210 (Feb. 2004).

Sanders, S. P. et al., "Role of Nasal Nitric Oxide in the Resolution of Experimental Rhinovirus Infection," Journal of Allergy and Clinical Immunology, vol. 113, No. 4, pp. 697-702 (Apr. 2004).

Schmidt, I. et al., Physiologic and Proteomic Evidence for a Role of Nitric Oxide in Biofilm Formation by *Nitrosomonas europaea* and Other Ammonia Oxidizers; Journal of Bacteriology, vol. 186, No. 9, pp. 2781-2788 (May 2004).

Reynolds, M. M., et al., "Nitric Oxide-Releasing Hydrophobic Polymers: Preparation, Characterization, and Potential Biomedical Applications," Free Radical Biology & Medicine, The Official Journal for the Society for Free Radical Biology and Medicine, vol. 37, No. 7, pp. 926-936 (Oct. 2004).

Lechner, M., et al., "Inducible Nitric Oxide Synthase (iNOS) in Tumor Biology: The Two Sides of the Same Coin," Seminars in Cancer Biology, vol. 15, pp. 277-289 (2005).

Ghaffair, A., et al., "A Direct Nitric Oxide Gas Delivery System for Bacterial and Mammalian Cell Cultures," Nitric Oxide Biology and Chemistry, vol. 12, pp. 129-140 (2005).

Proud, D., "Nitric Oxide and The Common Cold," Journal of Allergy and Clinical Immunology, vol. 5, pp. 37-42 (2005).

Nablo, B. J., et al., Inhibition of Implant-Associated Infections Via Nitric Oxide Release, Science Direct, Biomaterials, vol. 26, pp. 6984-6990 (May 2005).

McMullin, B. B., MSc RRT, et al., "The Antimicrobial Effect of Nitric Oxide on the Bacteria That Cause Nosocomial Pneumonia in Mechanically Ventilated Patients in the Intensive Care Unit," Respiratory Care, vol. 50, No. 11, pp. 1451-1456 (Nov. 2005).

Hurford, W. E.; Nitric Oxide As A Bacterial Agent: Is the Cure Worse Than the Disease?; Respiratory Care, vol. 50, No. 11, pp. 1428-1429 (Nov. 2005).

Katayama, Y. et al., "A Minimal Dose of Inhaled Nitric Oxide Delivered As a 'Spike' of Small Volume in Early Inhalation," Section of Respiratory Medicine, Division of Clinical Sciences, The Medical School, University of Sheffield (23 pages).

Turchi, J. J., "Nitric Oxide and Cisplatin Resistance: NO Easy Answers," PNAS, vol. 103, No. 12, pp. 4337-4338 (Mar. 21, 2006).

Hagenah, Jens-Uwe, "The Use of Nitric Oxide (NO) in Intensive Care Ventilation," *Dragerwerk Aktiengesellscha*, pp. 1 and 3-36 (Apr. 25, 1995).

Miller, C., et al., "Gaseous nitric oxide bactericidal activity retained during intermittent high-does short duration exposure," *Nitric Oxide* 20:16-23 (2009).

Hergott, C.A., et al., "Effects of Continuous vs Pulsed Inhaled Nitric Oxide in a Rat Model of *Pseudomonas aeruginosa* Pneumonia," poster presented to the American Thoracic Society International Conference 2006 (May 21, 2006).

Hergott, C.A., et al., "Effects of Effects of Continuous vs Pulsed Inhaled Nitric Oxide in a Rat Model of *Pseudomonas aeruginosa* Pneumonia," unpublished manuscript submitted to the American Thoracic Society.

Hurford, W., "Nitric Oxide As a Bactericidal Agent: Is the Cure Worse Than the Disease?" *Respiratory Care*, vol. 50, No. 11:1428-29 (Nov. 2005).

Fang, Ferric C., "Mechanisms of Nitric Oxide-related Antimicrobial Activity," Journal of Clinical Investigations, vol. 99, No. 12, 2818-2825 (Jun. 1997).

Miller, Christopher C., "The Antibacterial Role of Exogenous Nitric Oxide Gas" (copyright Nov. 2004).

Ghaffari, A., et al., "A direct nitric oxide gas delivery system for bacterial and mammalian cell cultures," Nitric Oxide, 12:129-40 (2005).

Supplementary European Search Report for Application 05747498.3, Feb. 18, 2010, Sensormedics Corporation, et al.

* cited by examiner

INTERMITTENT DOSING OF NITRIC OXIDE
GAS

This application is a continuation of PCT Application No. PCT/US05/016427, filed May 11, 2005, which claims priority to U.S. Provisional Application No. 60/570,429, filed May 11, 2004.

FIELD OF THE INVENTION

The field of the present invention relates to methods and devices for delivery of exogenous or gaseous nitric oxide gas to mammals.

BACKGROUND OF THE INVENTION

NO is an environmental pollutant produced as a byproduct of combustion. At extremely high concentrations (generally at or above 1000 ppm), NO is toxic. NO also is a naturally occurring gas that is produced by the endothelium tissue of the respiratory system. In the 1980's, it was discovered by researchers that the endothelium tissue of the human body produced NO, and that NO is an endogenous vasodilator, namely, an agent that widens the internal diameter of blood vessels.

With this discovery, numerous researchers have investigated the use of low concentrations of exogenously inhaled NO to treat various pulmonary diseases in human patients. See e.g., Higenbottam et al., Am. Rev. Resp. Dis. Suppl. 137:107, 1988. It was determined, for example, that primary pulmonary hypertension (PPH) can be treated by inhalation of low concentrations of NO. With respect to pulmonary hypertension, inhaled NO has been found to decrease pulmonary artery pressure (PAP) as well as pulmonary vascular resistance (PVR). The use of inhaled NO for PPH patients was followed by the use of inhaled NO for other respiratory diseases. For example, NO has been investigated for the treatment of patients with increased airway resistance as a result of emphysema, chronic bronchitis, asthma, adult respiratory distress syndrome (ARDS), and chronic obstructive pulmonary disease, (COPD). In 1999, the FDA approved the marketing of nitric oxide gas for use with persistent pulmonary hypertension in term and near term newborns. Because the withdrawal of inhaled nitric oxide from the breathing gas of patients with pulmonary hypertension is known to cause a severe and dangerous increase in PVR, referred to as a "rebound effect", nitric oxide must be delivered to these patients on a continuous basis.

In addition to its effects on pulmonary vasculature, NO may also be introduced as a anti-microbial agent against pathogens via inhalation or by topical application. See e.g., WO 00/30659, U.S. Pat. No. 6,432,077, which are hereby incorporate by reference in their entirety. The application of gaseous nitric oxide to inhibit or kill pathogens is thought to be beneficial given the rise of numerous antibiotic resistant bacteria. For example, patients with pneumonia or tuberculosis may not respond to antibiotics given the rise of antibiotic resistant strains associated with these conditions.

Clinical use of nitric oxide for inhalation has conventionally been limited to low concentration of nitric oxide given the potential toxicity. The toxicity may stem from binding of nitric oxide to hemoglobin that give rise methemoglobin or from the conversion of nitric oxide gas to nitrogen dioxide ($NO_2$). However, to overwhelm pathogenic defense mechanisms to nitric oxide, it is desirable to deliver nitric oxide at a higher concentration (e.g., between 150 ppm to 250 ppm, and even to 400 ppm) than has traditionally been used clinically for inhalation. Thus, a need exists for a delivery method that is effective against combating pathogens and minimizing the risk of toxicity.

SUMMARY OF THE INVENTION

It is envisioned that a method and device delivering intermittent high doses of nitric oxide for a period of time and which cycles between high and low concentration of nitric oxide is desirable, useful, and overcomes the problems of toxicity. The high concentration of nitric oxide is preferably delivered intermittently for brief periods of time that are interspersed with periods of time with either no nitric oxide delivery or lower concentrations of nitric oxide. This keeps the exposure to the high concentrations of nitric oxide required to overwhelm the nitric oxide defense mechanisms of the pathogens to an average level that is safe for humans to inhale.

In a preferred embodiment, high concentration of nitric oxide may be delivered at a concentration between 80 ppm to 300 ppm, preferably between 150 ppm to 250 ppm, and more preferably between 160 ppm to 200 ppm. Low concentration of nitric oxide preferably is delivered at a concentration between zero (0) ppm to 80 ppm, and preferably at a concentration of 20 ppm to 40 ppm.

The time periods may vary and in a wide range that preferably will deliver a dose of x time of 600 to 1000 ppmhrs per day. For example, the method would deliver 160 ppm for 30 minutes every four hours with 20 ppm delivered for the 3.5 hours between the higher concentration delivery. High concentration may also be delivered for a period of time between 10 minutes to 45 minutes, and the low concentration is preferably delivered for a period of time longer than the period of time in which the high concentration is delivered. However, it may also be delivered for the same length of time as the high concentration of nitric oxide with less number of cycles to achieve substantially the same amount of ppmhrs of nitric oxide per day. Thus, the high and low concentrations are alternately delivered, and the cycling of the delivery can be for a day, two days, three days, or any other time prescribed by a physician.

Devices for the delivery of nitric oxide are commercially available and may include continuous flow devices, flow matching devices, or pulse dose devices. For example, the FDA has already approved three different nitric oxide delivery systems in the United States: AeroNOx® Delivery System and the ViaNOx DS System (Pulmonox, Canada) and the INOvent® Delivery System (Datex-Ohmeda, Wis.). Other devices have also been described in literature and various publications and patents (e.g., U.S. Pat. No. 6,581,599, which is incorporated here by reference in its entirety).

In another aspect of the invention, the device for use to deliver intermittent high doses of nitric oxide may include a source of nitric oxide gas (e.g., nitric oxide gas in compressed gas cylinders), controller (e.g. an electronic controller or microprocessor), nitric oxide analyzer, and timer in which the concentration of nitric oxide delivered is automatically changed on a timed basis to a concentration set by the operator and for a set period of time defined by the operator. The device would include logic (e.g. software or firmware) that allows for setting of two different nitric oxide concentrations and with separate time settings for the delivery of each concentration. The device may also include gas mixers (such as gas blenders or combinations of flow control valves and T or Y shaped tube connections), tubings, a source of diluent gas (e.g. room air, oxygen, or inert gas), and electronically regulated needle valves or other valve mechanism for controlling the release of nitric oxide gas, or the diluent gas, or both.

Alternatively, the device may also include two sources of nitric oxide gas, in which one source provides the high concentration of nitric oxide and the other source provides the low concentration of nitric oxide. A switch valve (preferably electronically controlled) is then provided to switch the flow of nitric oxide gas from the high concentration to the low concentration, or vice versa, based on a predefined time. A third source of diluent gas may also be provided to dilute the nitric oxide gas.

DETAILED DESCRIPTION OF THE PREFERRED EMBODIMENTS

It is currently believed that at higher concentration, nitric oxide gas overwhelms the defense mechanism of pathogens that use the mammalian body to replenish their thiol defense system. The 20 thiol defense system may include for example, the mycothiol for mycobacterium or glutathione for other bacteria. Once this defense mechanism is depleted, the pathogen is defenseless against the killing effects of nitric oxide. A lower dose or concentration of nitric oxide gas delivered in between the bursts of high concentration nitric oxide maintains nitrosative stress pressure on the pathogens to prevent them from rebuilding their defense system to an adequate level. Thus, a preferred therapeutic or delivery profile for combating pathogens may comprise the delivery of a first concentration of nitric oxide gas for a number of time periods interspersed with intervals in between wherein a second concentration of nitric oxide is administered during the intervals. The first concentration is preferably at a high concentration sufficient to kill or inhibit microbial growth. For example, the first concentration may range from about 80 ppm to 400 ppm, more preferably between 150 to 250 ppm and most preferably between 160 ppm to 200 ppm.

The second concentration is preferably at low concentration of nitric oxide gas such as ranging from 20 to 80 ppm. Alternatively, it should also be understood that the second concentration can also be zero ppm or close to trace amount of nitric oxide gas.

Figure 1:
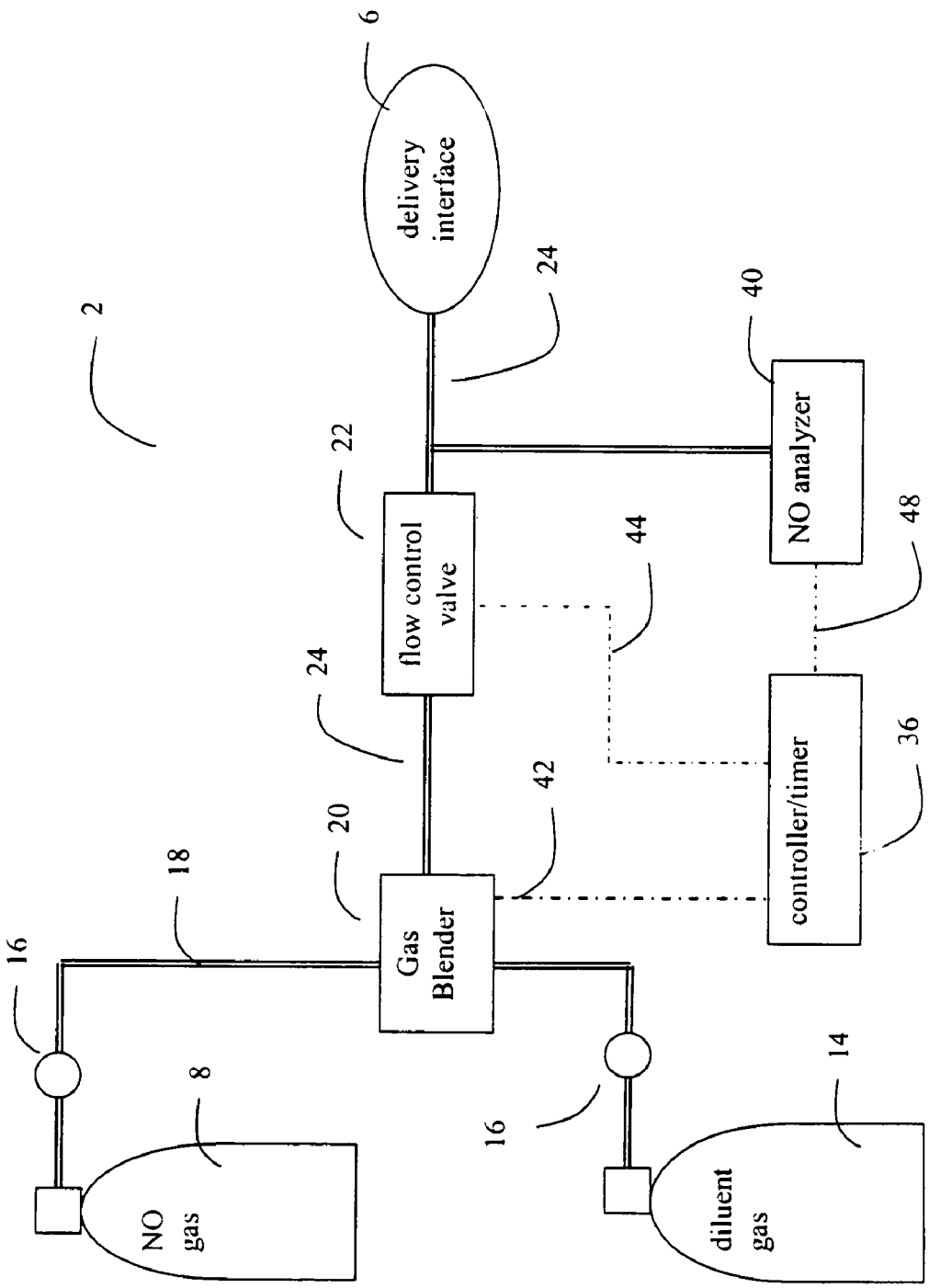
FIGS. 1-3 illustrate schematic representations of various embodiments of a nitric oxide delivery device according to one aspect of the present invention.
Figure 2:
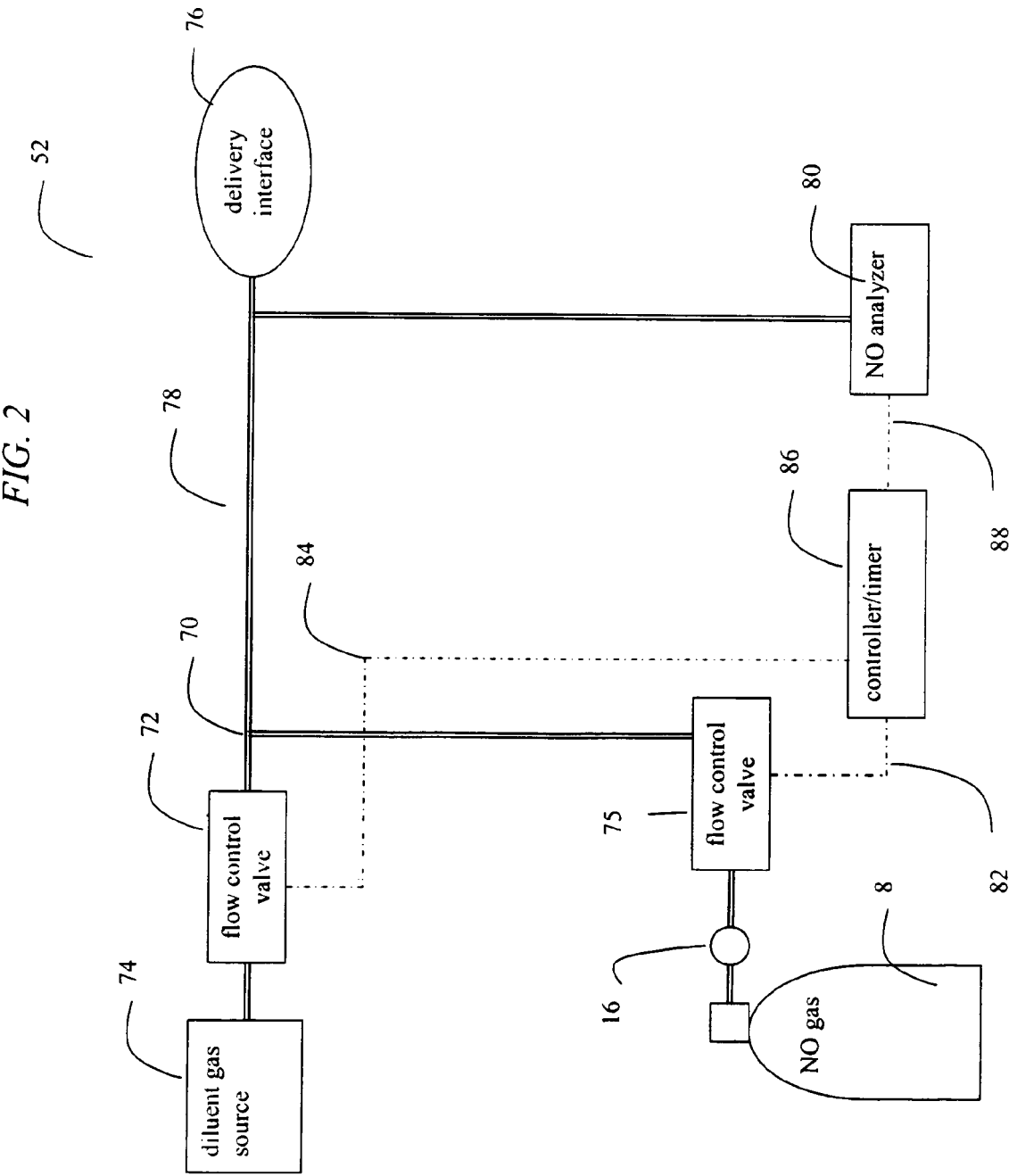
Figure 3:
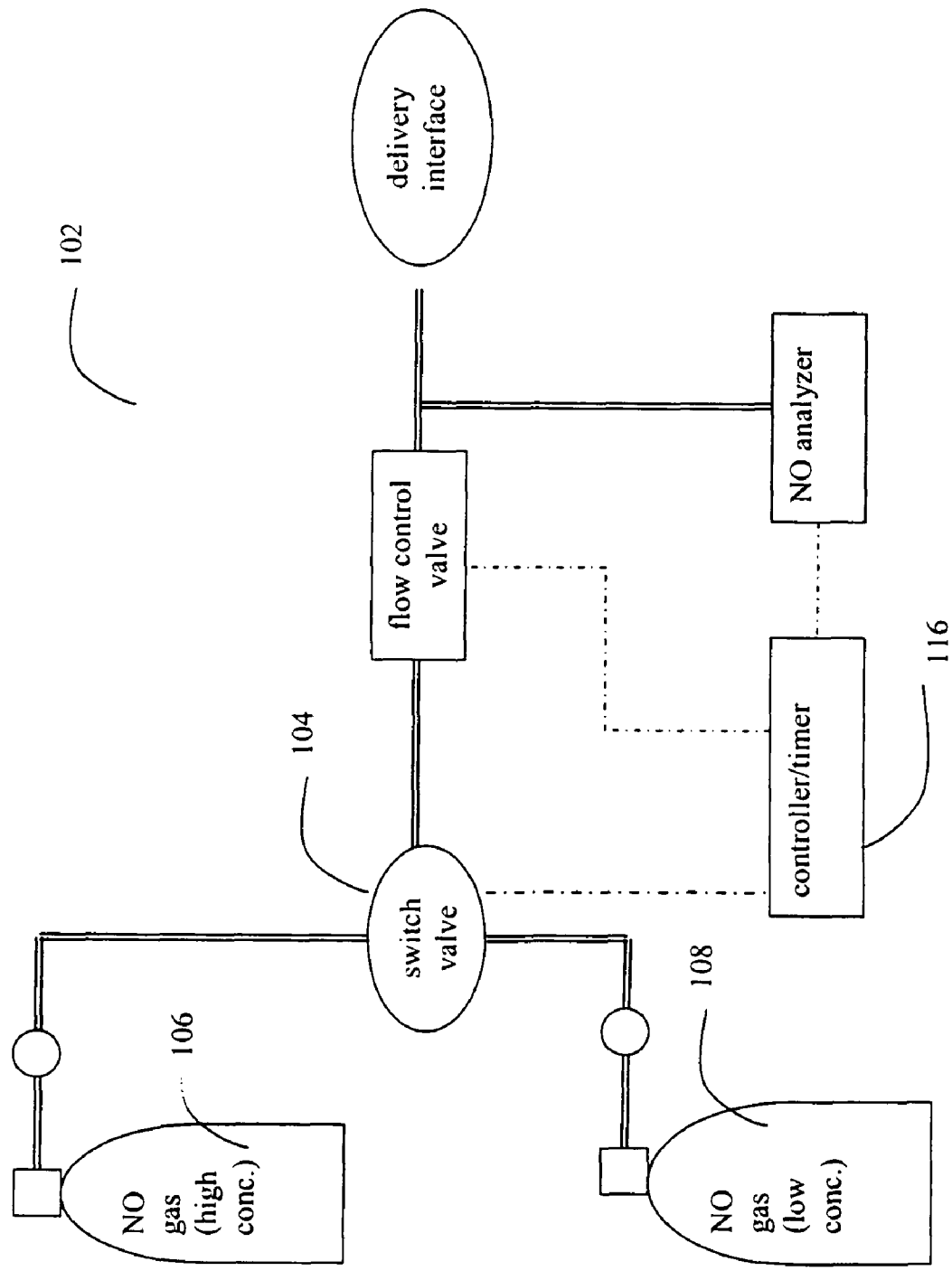

Turning now to the figures, FIGS. 1-3 illustrate various embodiments of a nitric oxide delivery device for use with the present invention. FIG. 1 shows, in its most general sense, a NO delivery device 2 that includes a source of nitric oxide gas 8 adapted for delivery of the NO gas to a mammal through a delivery interface 6. FIG. 1 illustrates one preferred embodiment of the invention.

In FIG. 1, the NO gas source 8 is a pressurized cylinder containing NO gas. While the use of a pressurized cylinder is the preferred method of storing the NO-containing gas source 8, other storage and delivery means, such as a dedicated feed line (wall supply) can also be used. Typically, the NO gas source 8 is a mixture of $N_2$ and NO. While $N_2$ is typically used to dilute the concentration of NO within the pressurized cylinder, any inert gas can also be used. When the NO gas source 8 is stored in a pressurized cylinder, it is preferable that the concentration of NO in the pressurized cylinder fall within the range of about 800 ppm to about 10,000 ppm. Commercial nitric oxide manufacturers typically produce nitric oxide mixtures for medical use at around the 1000 ppm range. Pressurized cylinders containing low concentrations of NO (e.g., less than 100 ppm NO) can also be used in accordance with the device and method disclosed herein. Of course, the lower the concentration of NO used, the more often the pressurized cylinders will need replacement.

FIG. 1 also shows a source of diluent gas 14 as part of the NO delivery device 2 that is used to dilute the concentration of NO. The source of diluent gas 14 can contain $N_2$, $O_2$, Air, an inert gas, or a mixture of these gases. It is preferable to use a gas such as $N_2$ or an inert gas to dilute the NO concentration at lower concentration since these gases will not oxidize the NO into $NO_2$ as would $O_2$ or air. Nevertheless, for inhalation applications for delivery of high concentration of NO where higher concentration of nitrogen may already be present, the NO flow may be supplemented or diluted with oxygen to prevent the displacement of oxygen by nitrogen that may lead to asphyxiation. It is preferred, especially when delivering higher concentration of NO gas that delivery line downstream of the injection site or gas blender be minimized to reduce the risk of formation of $NO_2$.

The source of diluent gas 14 is shown as being stored within a pressurized cylinder. While the use of a pressurized cylinder is shown in FIG. 1 as the means for storing the source of diluent gas 14, other storage and delivery means, such as a dedicated feed line (wall supply) can also be used. The source of diluent gas can also be a ventilator, air pump, blower, or other mechanical device that moves breathable air.

The NO gas from the NO gas source 8 and the diluent gas from the diluent gas source 14 preferably pass through pressure regulators 16 to reduce the pressure of gas that is admitted to the NO delivery device 2. The respective gas streams pass via tubing 18 to a gas blender 20. The gas blender 20 mixes the NO gas and the diluent gas to produce a NO-containing gas that has a reduced concentration of NO compared to NO gas contained in the source 8. Preferably, a controller 36 controls the gas blender through electrical connection line 42 such that gas blender can be set to mix the gases to the desired NO concentration (e.g., 160 ppm-200 ppm for the high concentration period, and 20-40 ppm for the low concentration period) and output via tubing 24.

An optional flow control valve 22 can be located downstream of the gas blender 20 to control the flow of the NO gas to the delivery interface 6. The flow control valve 22 can include, for example, a proportional control valve that opens (or closes) in a progressively increasing (or decreasing if closing) manner. As another example, the flow control valve 22 can include a mass flow controller. The flow control valve 22 controls the flow rate of the NO-containing gas that is input to the delivery device 6.

The delivery interface 6 can be any type of interface adaptable for delivery of the gas to a mammal. For example, if the NO gas is to be delivered to the mammal's airways or lungs, the delivery interface 6 may include a facial mask, nasal insert, or endotracheal tube that interface with the mammal's respiratory system. It should be understood that the types of delivery interface 6 should not be limiting and depends on the specific applications and locations for the delivery of the gas. In another example, if the NO gas is to be delivered topically to a surface of the body such as a skin or eye, a surface of an organ such heart, stomach, etc., a bathing unit as described in U.S. Pat. No. 6,432,077, issued to one of the inventors may be used. U.S. Pat. No. 6,432,077 is hereby incorporated by reference as if fully set forth herein. Still further example of a delivery interface 6 may an interface to a dialysis circuit or extracorporeal circuitry wherein the NO gas is delivered directly to the blood or body fluids so as to expose the blood or body fluids to NO gas. Such delivery interface are described, for example, in U.S. patent application Ser. No. 10/658,665, filed on Sep. 9, 2003, which is hereby incorporated by reference in its entirety.

Still referring to FIG. 1, the delivery device 2 preferably includes a controller 36 that is capable of controlling the flow control valve 22 and the gas blender 20. The controller 36 is preferably a microprocessor-based controller 36 that is connected to an input device (not shown). The input device may be used by an operator to adjust various parameters of the delivery device such as NO concentration and therapy/exposure time periods. An optional display can also be connected with the controller 36 to display measured parameters and settings such as the set-point NO concentration, the concentration of NO flowing to the delivery interface 6, the concentration of $NO_2$, the flow rate of gas into the delivery interface 6, the total time of therapy/delivery, and/or the number of cycles for alternating between high and low concentrations of NO gas.

Figure 4:
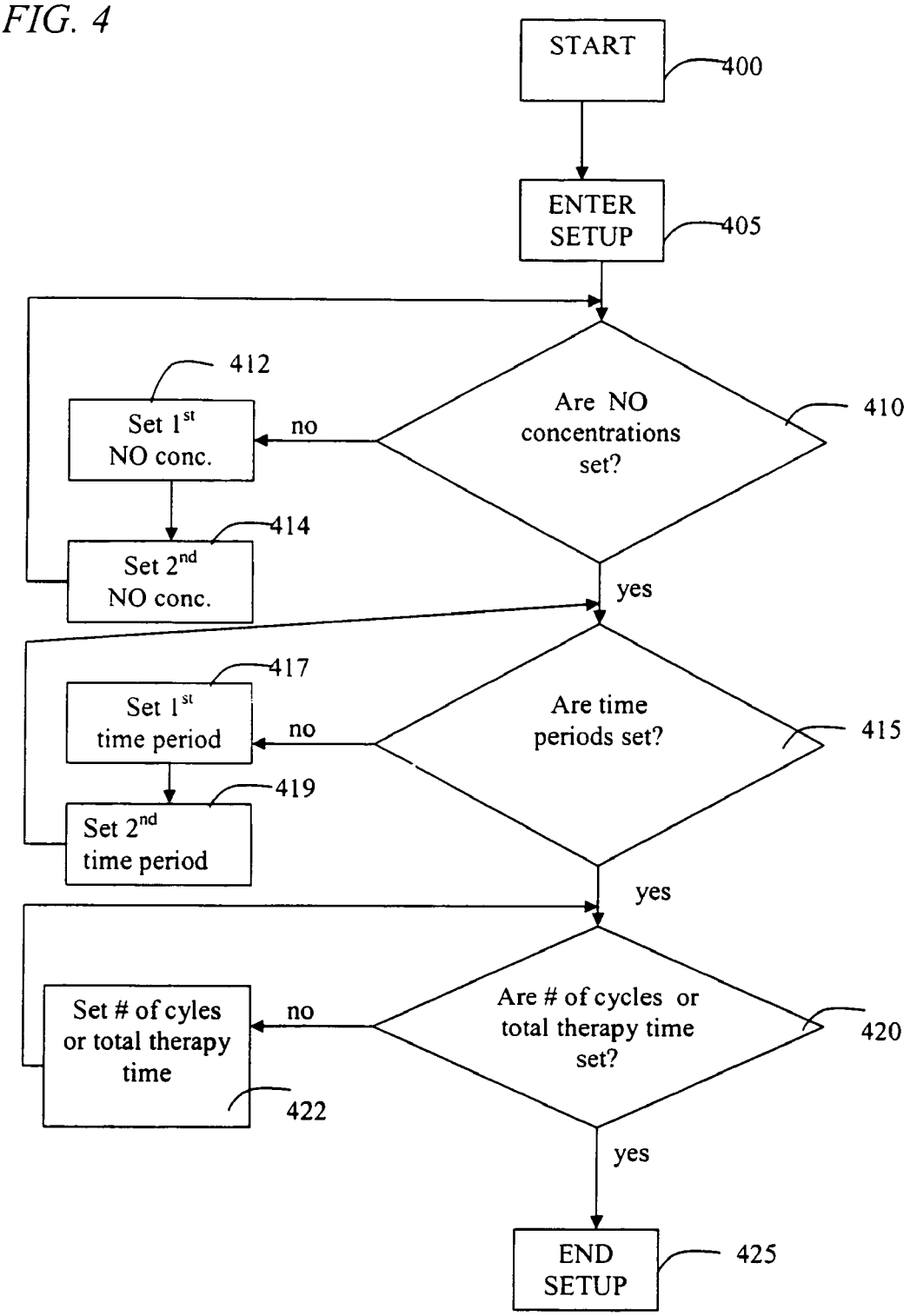
FIG. 4 illustrates the logic for setting the alternating delivery profile for high and low concentrations of nitric oxide gas.
Figure 5:
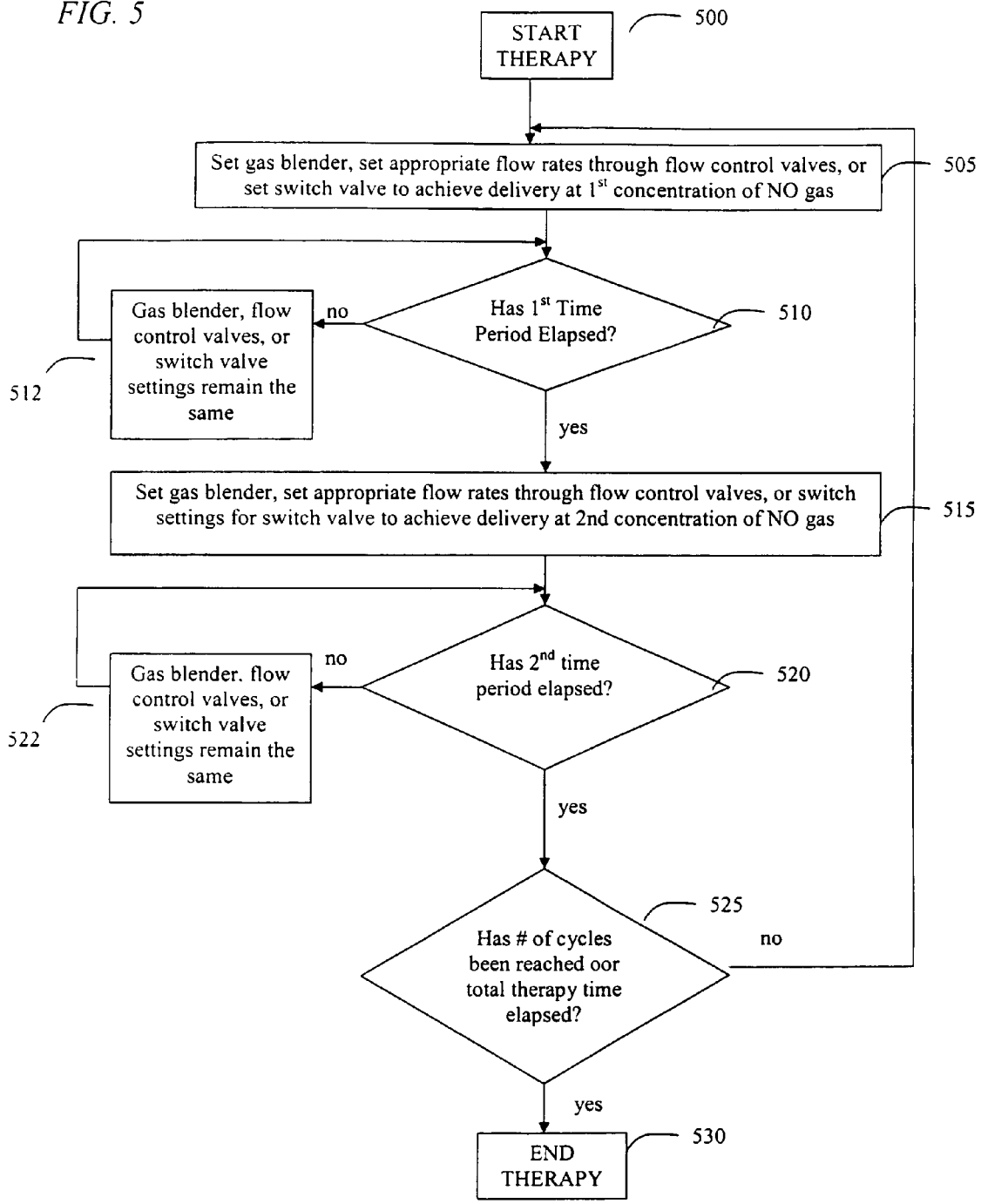
FIG. 5 illustrates the logic for delivering alternating high and low concentrations of nitric oxide gas.
Figure 6:
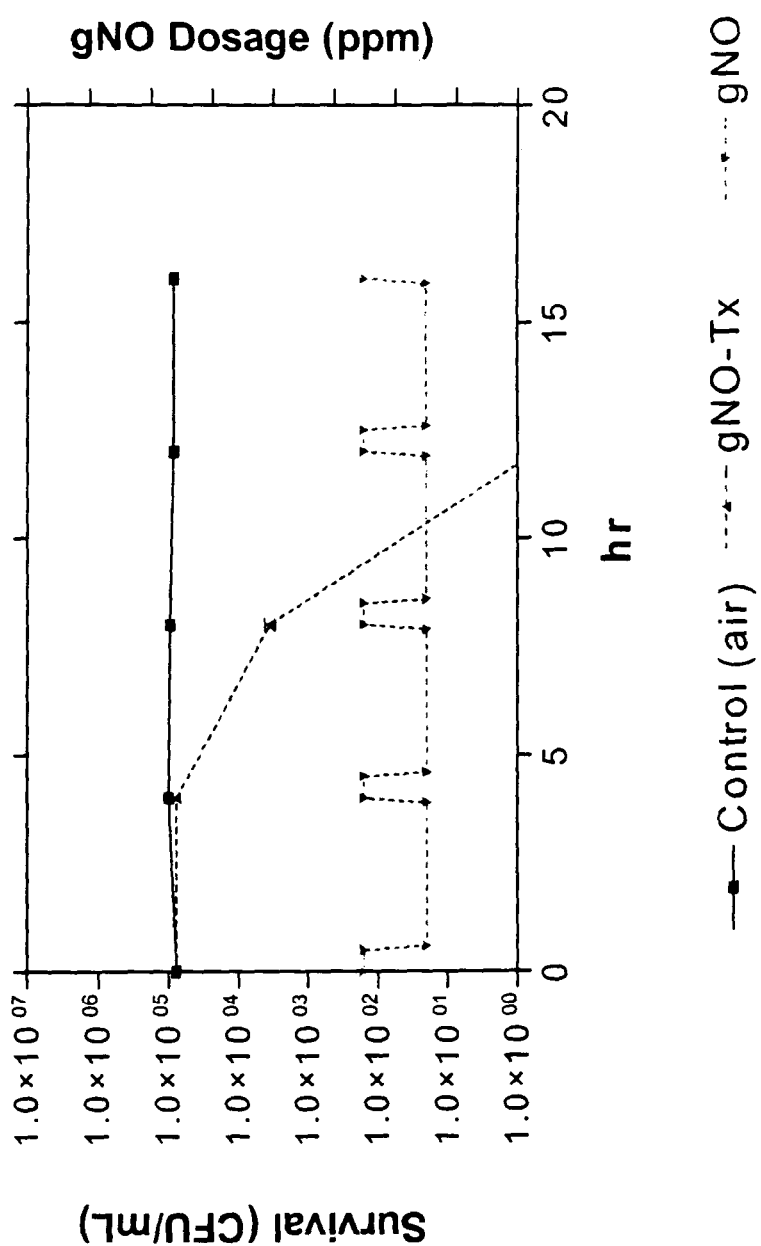
FIG. 6 shows the effect on survival of *S. aureus* (ATCC#25923) when alternately exposed to NO gas (gNO) exposure at 160 ppm nitric oxide gas for 30 minutes and 20 ppm for 3.5 hours for a total exposure time of 24 hours.
Figure 7:
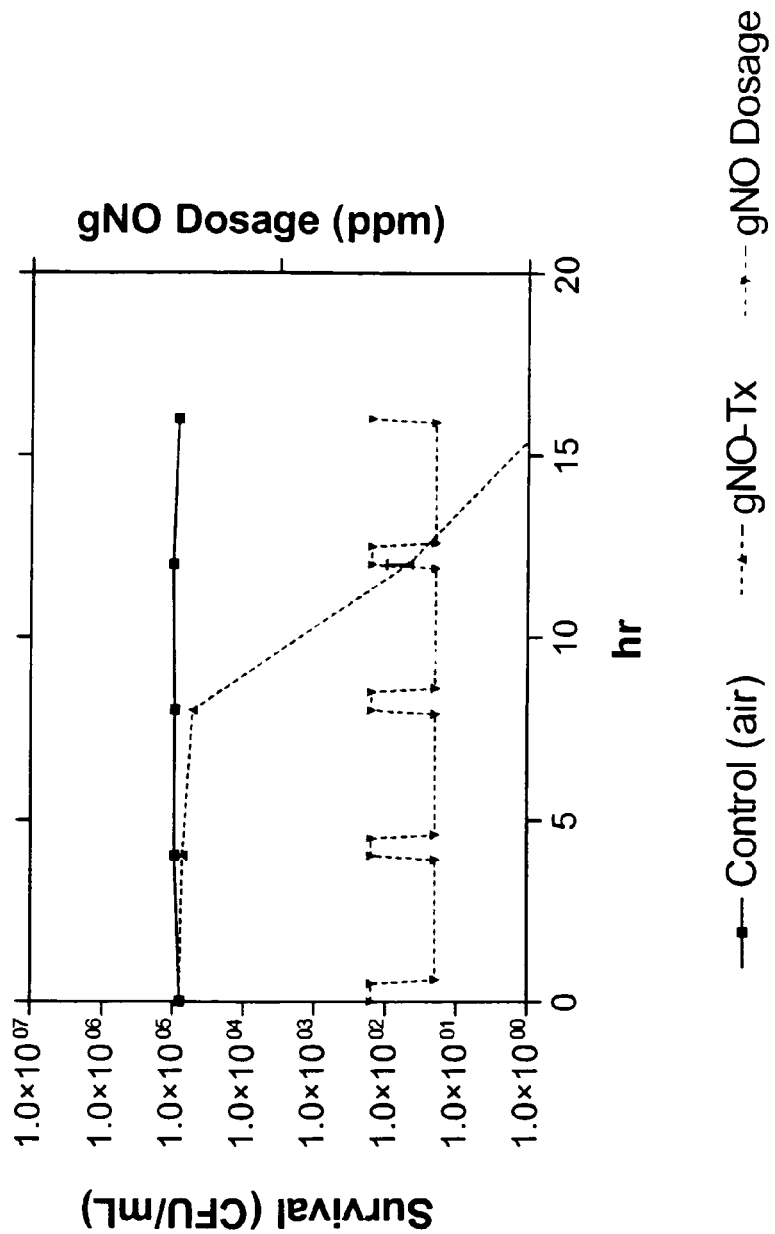
FIG. 7 shows the effect on survival of *P. aeruginosa* (ATCC#27853) when alternately exposed to NO gas (gNO) exposure at 160 ppm nitric oxide gas for 30 minutes and 20 ppm for 3.5 hours for a total exposure time of 24 hours.
Figure 8:
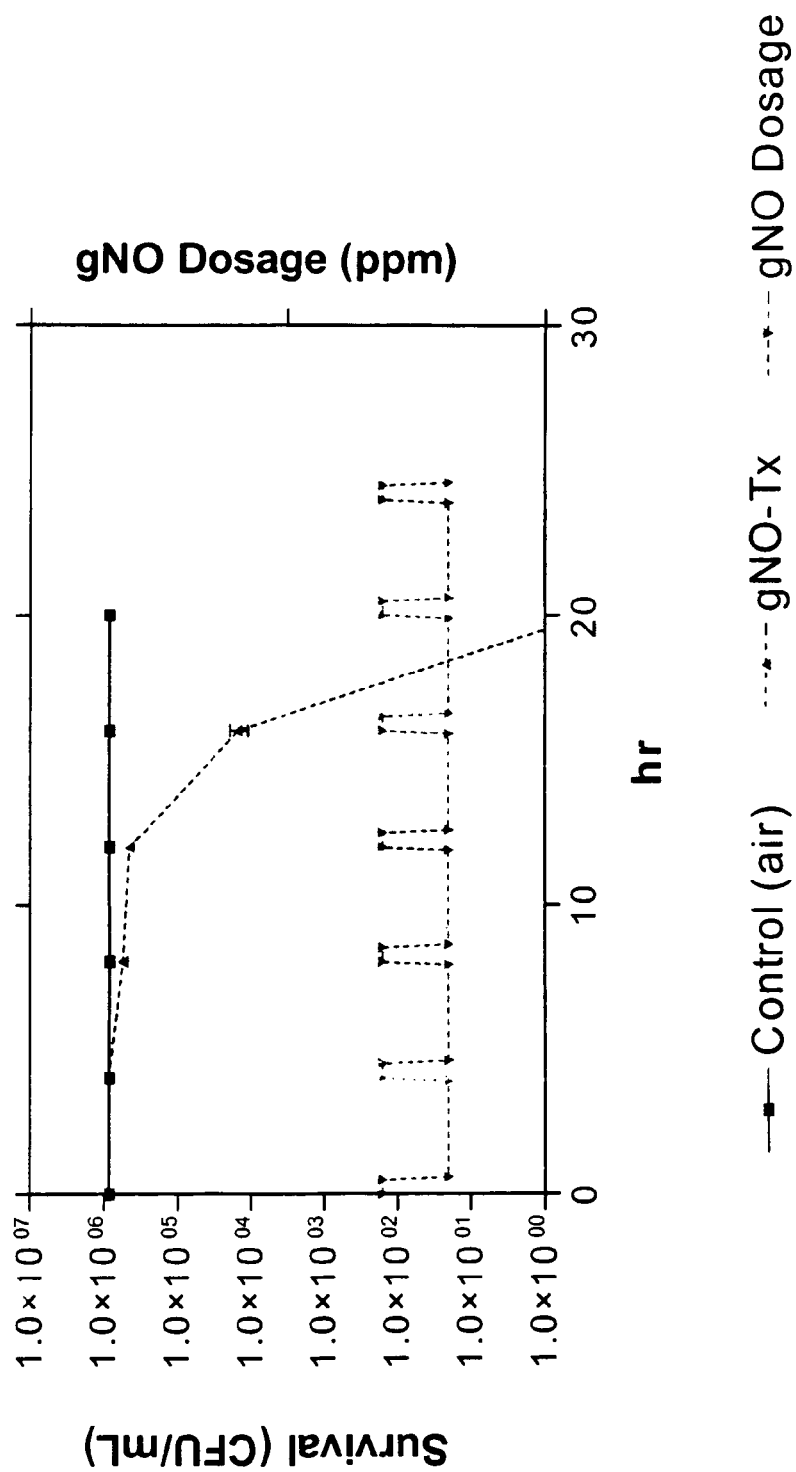
FIG. 8 shows the effect on survival of *P. aeruginosa* (clinical strain from Cystic Fibrosis) when alternately exposed to NO gas (gNO) exposure at 160 ppm nitric oxide gas for 30 minutes and 20 ppm for 3.5 hours for a total exposure time of 24 hours.
Figure 9:
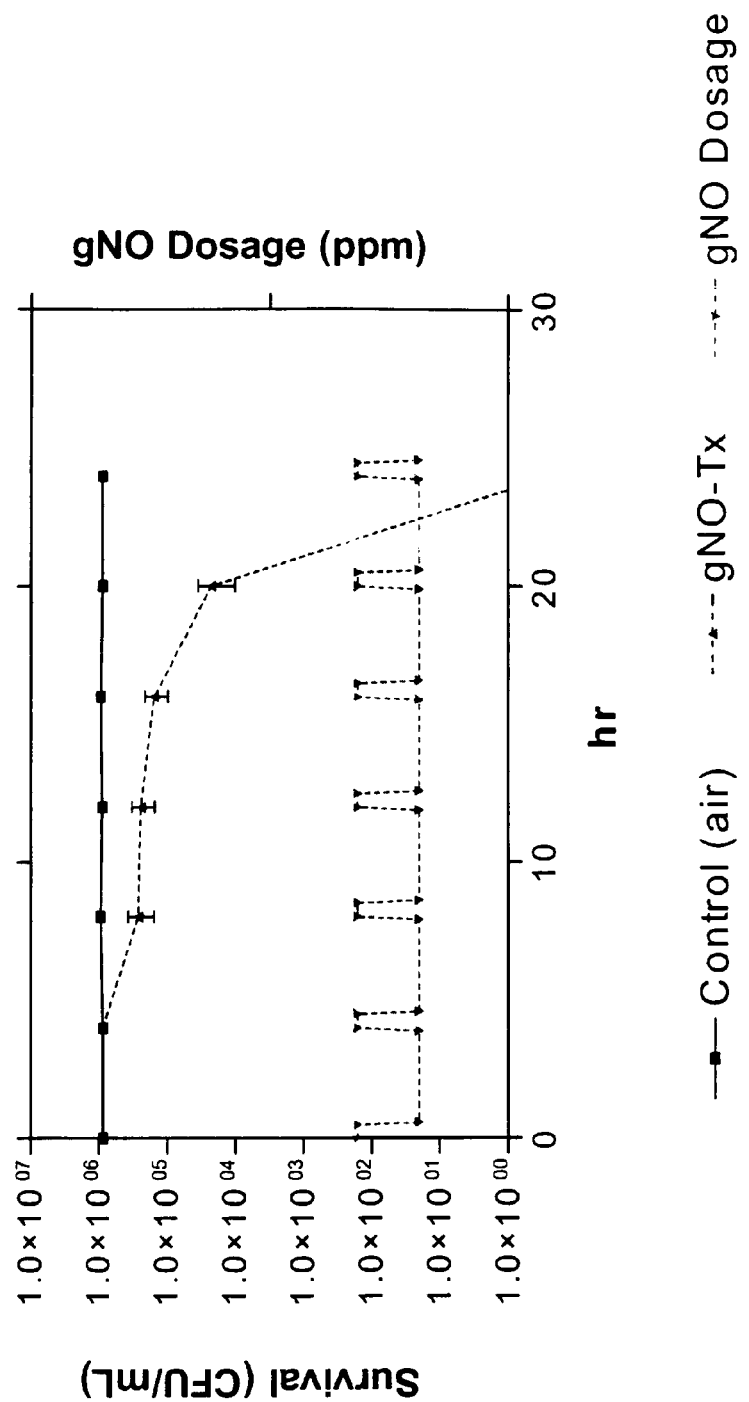
FIG. 9 shows the effect on survival of *E. coli* when alternately exposed to NO gas (gNO) at 160 ppm nitric oxide gas for 30 minutes and 20 ppm for 3.5 hours for a total exposure time of 24 hours.

The controller preferably includes a timer for counting down the time periods of the NO gas delivery at the different concentrations. Moreover, the controller preferably includes logic such as firmware or software programs for executing the alternate delivery of high and low concentration of NO gas at pre-set or user programmable time periods. The processes for execution by such logic are illustrated in FIGS. 4 and 5.

The controller 36 also preferably receives signals through signal line 48 from NO analyzer 40 regarding gas concentrations if such analyzer 40 are present within the delivery device 2. Signal lines 42 and 44 are connected to the gas blender 20 and flow control valve 22 respectively for the delivery and receipt of control signals.

In another embodiment of the nitric oxide delivery device, the controller 36 may be eliminated entirely and the gas blender 20 may be set manually at the desired high or low concentration of nitric oxide gas. The time period may also be tracked manually and at the appropriate set time period, the gas blender is adjusted to either increase to the high concentration NO gas or decrease to the low concentration NO gas. The flow rate of the gas into the delivery interface 6 may be pre-set or adjusted manually.

FIG. 2 shows an alternative embodiment of a nitric oxide delivery device 52 in which the desired concentration of NO gas is achieved by mixing with a T or Y shaped connection 70 based on the flow rates of the NO gas flowing from the NO gas source 8 and the diluent gas flowing from the diluent gas source 74. The respective flow rates are controlled via the flow control valves 72 and 75. Mixing of the gases starts at the T or Y shaped connection point 70 and continues through the delivery line 78. An NO analyzer 80 samples the gas mixture at a juncture close to the delivery interface to determine the NO concentration of the gas mixture flowing to the delivery interface 76. The measured NO concentration is then fed back through signal line 88 to the controller 86, which in turn processes the information by comparing the measured NO concentration with the set desired NO gas concentration. The controller 86 then adjusts the flow control valves 72 and 75, if appropriate, by sending control signals through lines 82 and 84 such that the flow rate(s) may be adjusted in order to achieve the desired concentration of NO gas flowing to the delivery interface 76. It should be understood that the controller 86 may similarly include all the features discussed above in connection with controller 36 in FIG. 1. Likewise, the delivery interface 76 may be adapted similarly to the delivery interface 6, as described in connection with FIG. 1.

FIG. 3 illustrates yet another embodiment of a nitric oxide delivery device in accordance to one aspect of the present invention. In this delivery device 102, instead of having gas mixers (e.g., gas blender or T or Y-shaped connection), the delivery device 102 utilizes a switch valve 104 to switch between a high concentration NO gas source 106 and a low concentration NO gas source 108. The switch valve 104 is controlled by the controller 116 that at the appropriate time switches between the high and low concentration of NO gas according to the present invention. It should be understood that the low concentration NO gas source 108 can also be replaced with non-NO gas source such as air, if the desired period of low NO concentration is zero ppm of NO gas.

Referring now to FIGS. 4 and 5, process flows are exemplified that may be executed by logic (firmware or software) programmed into the controllers 36, 86, and 116. FIG. 4 illustrates a process flow for setting up the desired concentrations and time periods for NO gas delivery starting from Step 400 "START." At Step 405, the logic enters the setup subroutine for setting the desired NO concentrations and time periods. At Step 410, the logic verifies if there are concentration values set for the NO delivery profile. If values are already set, then the process proceeds to Step 415 to verify the values set for the time periods of delivery. If no values have yet been set for the NO concentrations, then the logic calls a subprocess comprising of steps 412 and 414 is called to set the $1^{st}$ and $2^{nd}$ NO concentration for the therapeutic profile to be delivered. For example, the $1^{st}$ NO concentration may be set for about 160 ppm to 300 ppm of NO gas to be delivered and the $2^{nd}$ concentration may be set for 0 ppm to 80 ppm of NO gas to be delivered. The values of the NO concentrations set are then used by the controller to set the gas blender or the flow control valves in the process illustrated in FIG. 5.

After the values of NO concentrations have been set, the logic then proceeds to set the time periods for the delivery of the NO gas in Step 415. If the time periods have not yet been set, then a subprocess comprising steps 417 and 149 is called in which a first time period corresponding to the $1^{st}$ NO concentration and a $2^{nd}$ time period corresponding to the NO concentration are set.

After the values of NO concentrations and the time periods have been set, the logic then proceeds to set the number of cycles of alternating $1^{st}$ and $2^{nd}$ concentration of NO gas to be delivered. Alternatively, a total therapy time can be set in which the delivery of NO gas will cease at the end of the total therapy time. If the total therapy time or number of cycles have not been set, then a subprocess comprising of step 422 is called and these values are set. Afterwards, the setup process is ended and the device is ready to deliver NO gas for therapy.

FIG. 5 illustrates a process flow for execution by the logic in controller 36, 56, and 116, for the alternating delivery of high and low concentration of NO gas.

The START THERAPY in step 500 can be started once the NO gas delivery values in FIG. 4 has been entered. At Step 505, the controller 36 (FIG. 1) may then send a control signal through line 42 to the gas blender to set the appropriate gas blender settings to achieve the $1^{st}$ concentration of NO gas, the value of which was set in the setup process of FIG. 4. This process may also include feedback control from the NO analyzer 40 (FIG. 1) to the controller 36 such that the control of the gas blender may be fine tuned in that the actual NO gas concentration being delivered to the delivery interface 6 matches the set NO gas concentration.

Alternatively, the controller at Step 505 may send control signals to the flow control valves 72 and 75 (FIG. 2) to set the appropriate flow rates for the mixing of the gases to achieve the $1^{st}$ concentration set in the setup process of FIG. 4. This process may similarly include feedback control from the NO analyzer 80 (FIG. 2) to the controller 56. In yet another embodiment, the controller at Step 505 may set the switch valve 104 (FIG. 3) to select for delivery the NO gas from a source corresponding to the $1^{st}$ concentration of NO gas set in the setup process of FIG. 4.

Delivery of NO gas proceeds in accordance with the settings in Step 505. At step 510, the timer comprised in the controller 36, 56, or 116 compares the value of the $1^{st}$ time period set in FIG. 4 with the actual countdown in time. If the time period has not elapsed, then the gas blender, flow control valves, or switch valve settings remain the same in Step 512. If the $1^{st}$ time period has elapsed, then step 515 sets the gas blender, flow rates, or switch valve settings to that corresponding to the $2^{nd}$ concentration of NO gas, the value of which was set in the process of FIG. 4. Delivery of NO gas then proceeds on the $2^{nd}$ concentration until the $2^{nd}$ time period elapsed.

At the completion of the second time period, the logic proceeds to step 525 inquiring into whether the set number of cycles of total therapy time has elapsed. If the set number of cycles or total therapy time has been reached, the therapy ends in Step 530. Otherwise, the process repeats steps 505, 510, 515, and 525.

Further Examples of Delivery Methods

The implementation of the intermittent delivery of high doses of NO gas can be by many means. For example, delivery by inhalation or to the respiratory airway can be made to spontaneously breathing mammals or those managed with mechanical ventilation. With respect to spontaneously breathing mammals, delivery can be achieved via many of previously described gas delivery systems such as masks or nasal cannulas. The device for these mammals may include flowmeter or flow sensor to detect the onset of breathing (e.g., inhalation vs. exhalation) such that the nitric oxide gas would be delivered only when the mammal inhales. Mechanically ventilated mammals would have the nitric oxide delivered into the inspiratory limb of the ventilator circuit and may similarly be triggered only when the ventilator cycled a breath into the mammal.

In both of these implementations, the pattern of nitric oxide delivery may vary depending on the targeted location of the infection within the mammal's lungs and the desire to have the least concentration of nitric oxide residual in the delivery circuit. For example, if the infection were in the air sacs of the lungs, the nitric oxide could be turned off towards the end of the breath when the gas was going to be delivered only to the airways. As an alternative, if the infection were only in the airways, then the starting gas might have a lower concentration of nitric oxide.

Furthermore, it is preferred that the injection site for NO gas delivery be close to the patient's airway when using higher concentrations of NO gas so as to reduce the time for conversion to $NO_2$. This minimizes the dwell time of the NO gas in the delivery line before inhalation. Alternaively, the delivery system may utilize a bolus injection of a high concentration at a time point within the breath and allow the dilution of the NO to occur within the lungs.

While embodiments of the present invention have been shown and described, various modifications may be made without departing from the scope of the invention. The invention, therefore, should not be limited, except to the following claims, and their equivalents.

Experimental Results

The effectiveness of the intermittent high dose delivery of nitric oxide gas in combating microorganisms was tested and verified. Briefly, the experimental methods were as follows. Inoculums of varying bacteria was prepared to a suspension of $2.5 \times 10^8$ cfu/ml, and diluted 1:1000 in sterile normal saline. Three milliliters of the inoculums were used per well in a sterile culture place. Exposure of the inoculums were performed in an exposure chamber, which has been described for example, in Ghafarri, A. et al., "A direct nitric oxide gas delivery system for bacterial and mammalian cell cultures," Nitric Oxide. 12(3):129-40 (May 2005), which is hereby incorporated by reference as if fully set forth herein. The inoculums were exposed to 160 ppm of NO gas at a flow rate of 2.5 liters per minute for 30 minutes followed by exposure to 20 ppm of NO gas for 3.5 hours. The exposure to high and low concentrations of NO gas was repeatedly cycled every 4 hours for 24 hours. At various times (e.g., 0, 4, 8, and 12 hours), samples were taken and plated to determine the survivability of the bacteria as determined by counting cfu/ml.

FIGS. 6-9 show the survival of various bacteria used in the experiment with NO gas compared to exposure to air as control. As seen in these figures, cycling exposure to high and low concentrations of nitric oxide is an effective method of killing the bacteria. While it was observed that the effectiveness of cycling exposure to high and low concentrations over a longer period of time, was similar to that of continuous exposure to high concentration, cycling exposure provides a better safety profile in minimizing the risk of methemoglobin formation.

Additional studies were performed to test the hypothesis that the effect of NO gas in killing microorganisms is related to thiol function. Based on studies with various microorganisms, it was observed that Mycobacteria are less sensitive to NO gas damage. This may be due to Mycobacteria having an exceptional thiol, mycothiol, that maintains the redox balance in the cell and protects the cell from nitrosative and oxidative stress. In order to test this hypothesis, sensitivities to NO gas was compared between mycothiol-deficient *Mycobacterium smegmatis* Mutant MshA to its wild type counterpart, $mc^2$ 155 by exposing both strains to 200 ppm of NO gas. MshA is an enzyme needed in mycothiol biosynthesis.

Figure 10:
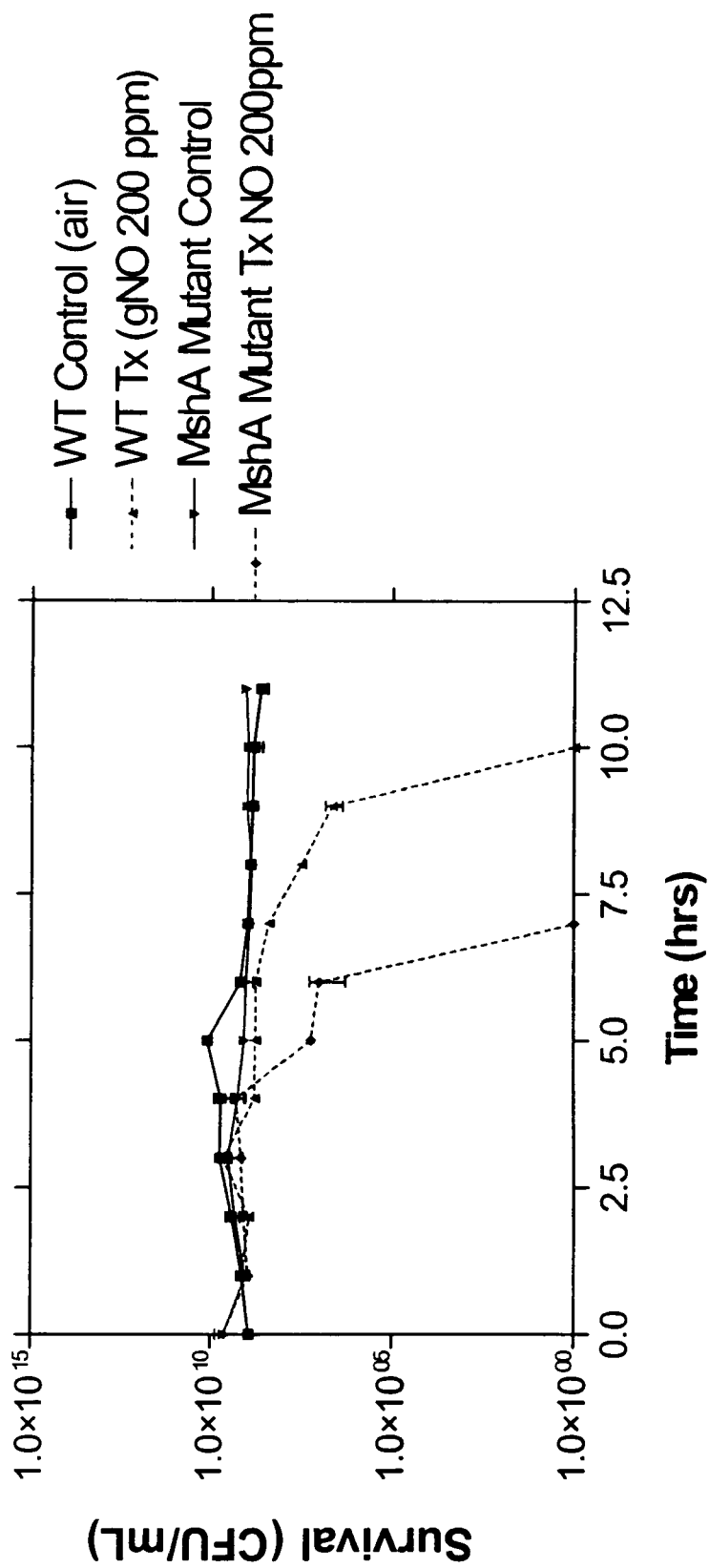
FIG. 10 shows the effect on survival of a MshA mycothiol deficient mutant *Mycobacterium smegmatis* and its wild type counterpart when exposed to 200 ppm NO gas (gNO).

FIG. 10 shows that the mycothiol-deficient MshA mutant was more sensitive to NO gas than its wild type counterpart and was killed in less time than its wild type counterpart.

Figure 11:
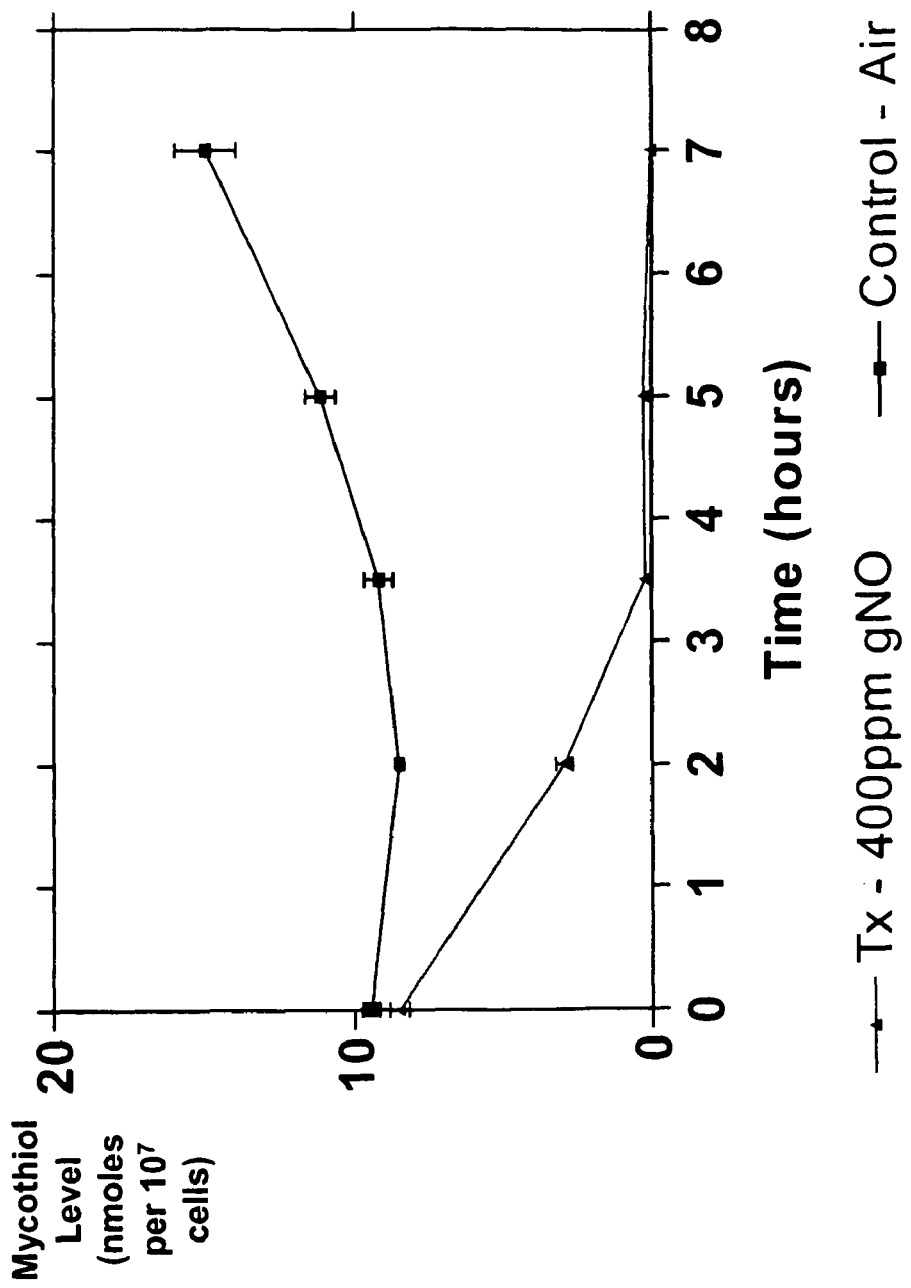
FIG. 11 shows the level of mycothiol in wild type *Mycobacterium smegmatis* when exposed to 400 ppm NO gas (gNO) compared to exposure to air.

Further experiments were conducted to assay and measure the mycothiol level using HPLC in wild type *M. smegmatis* after exposure to 400 ppm NO gas and were compared to mycothiol level after exposure to air. FIG. 11 shows that upon exposure to 400 ppm of NO gas, the level of mycothiol in the mycobacterium was reduced compared to exposure to air.

Thus, these results show the NO gas may likely act to deplete mycothiol, which is the mechanism by which the mycobacterium protects itself against oxidative stress.

In other bacteria, it is believed that the analogous molecule to mycothiol in mycobacteria is glutathione. The glutathione pool may normally act to protect the bacteria from endogenous NO and $H_2O_2$, which are released by macrophages against pathogens. Delivery of exogenous NO gas may thus act to overwhelm the glutathione pool, eliminating bacterial protection from $H_2O_2$, and binding iron based enzymes causing $O_2$ consumption cessation and electron transport center disruption and freeing metal ions into the bacterial cytosol. The free oxygen, metal ions, NO, and hydrogen peroxide further produce reactive nitrogen and oxygen species as well as metal ions that damage the bacteria's DNA by deamination. Thus, it is believed that cycling or alternating delivery of concentration of NO gas sufficient to overwhelm the glutathione defense mechanism for a period of time and a lower concentration of NO gas may be effective in combating microbes such as bacteria, mycobacteria, and fungi while at the same time exhibit a better safety profile.

Microbes may also include viruses. While viruses do not by themselves have thiol based detoxification pathways, they may still be inherently more susceptible to nitrosative stress. NO may inhibit viral ribonucleotide reductase, a necessary constituent enzyme of viral DNA synthesis and therefore inhibit viral replication. Nitric oxide may also inhibit the replication of viruses early during the replication cycle, involving the synthesis of vRNA and mRNA encoding viral proteins. With viruses also depending on host cells for detoxification of the body's defense pathways, the direct cytotoxic mechanisms of NO entering the host cells and the intracellular changes it produces, could also account for the viricidal effects through viral DNA deamination. Thus, it is believed that the cycling or alternating delivery of NO gas at high and low concentrations may also be effective against viruses.

What is claimed:

1. A method of topically delivering nitric oxide gas to a mammal to kill or inhibit the growth of microbes, the method comprising alternately administering at least a first concentration of nitric oxide gas and a second concentration of nitric oxide gas for a number of cycles, the first concentration applied topically for a first period of time sufficient to overwhelm the microbes' thiol defense mechanisms and kill or inhibit the growth of at least a portion of the microbes, and the second concentration lower than the first concentration and applied topically for a second period of time sufficient to maintain nitrosative stress on the microbes and interfere with replenishing the level of the microbes' thiol defense mechanisms, whereby the cycling of the first and second concentrations provides a cumulative killing of the microbes.

2. The method of claim 1 wherein the second period of time is longer than the first period of time.

3. The method of claim 1 wherein the first concentration of nitric oxide gas ranges from about 160 ppm to about 400 ppm.

4. The method of claim 3 wherein the second concentration of nitric oxide gas is less than about 80 ppm.

5. The method of claim 2 wherein the first period of time is about 30 minutes and the second period of time is about 3.5 hours.

6. A method of topically delivering nitric oxide gas to a mammal to kill or inhibit the growth of microbes, the method comprising topically administering to the mammal a first concentration of nitric oxide gas for a number of time periods that are interspersed with intervals in between wherein a second concentration of nitric oxide gas lower than the first concentration is topically administered during the intervals, wherein the first concentration of nitric oxide gas is sufficient to overwhelm the microbes' thiol defense mechanisms and kill or inhibit the growth of at least a portion of the microbes and the second concentration of nitric oxide gas is sufficient to maintain nitrosative stress on the microbes and interfere with replenishing the level of the microbes' thiol defense mechanisms, and whereby the topical administration of the first concentration and second concentration for a number of cycles provides a cumulative killing of the microbes.

7. The method of claim 6 wherein the first concentration of nitric oxide gas ranges from about 160 ppm to about 400 ppm.

8. The method of claim 7 wherein the second concentration of nitric oxide gas is less than about 80 ppm.

9. The method of claim 6 wherein the microbes are selected from a group consisting of bacteria, mycobacteria, viruses and fungi.

10. A device for delivery of nitric oxide gas to kill or inhibit the growth of microbes comprising:
a source of nitric oxide gas;
a source of diluent gas;
a delivery interface adaptable for topical delivery of the gases to a mammal;
a gas mixer downstream of the sources of nitric oxide gas and diluent gas and upstream of the delivery interface for mixing the nitric oxide gas with the diluent gas;
a controller that communicates with the gas mixer wherein the controller comprises logic for setting a nitric oxide gas delivery profile comprising at least a first concentration of nitric oxide gas sufficient to overwhelm the microbes' thiol defense mechanisms and kill or inhibit the growth of at least a portion of the microbes and a second concentration of nitric oxide gas sufficient to maintain nitrosative stress on the microbes and interfere with replenishing the level of the microbes' thiol defense mechanisms, and for automatically switching between the at least first and second concentrations of nitric oxide gas on a timed basis for a number of cycles, whereby the cycling of the first and second concentrations provides a cumulative killing of the microbes.

11. The device of claim 10 wherein each cycle comprises at least first and second time periods corresponding respectively to delivery of the first and second concentrations of nitric oxide gas.

12. The device of claim 11 wherein, in each cycle, the first time period is shorter than the second time period.

13. The device of claim 10 wherein the gas mixer comprises a T or Y shaped tubing connection and a flow control valve.

14. The device of claim 10 wherein the gas mixer comprises a gas blender.

15. The device of claim 10 wherein the delivery interface comprises a bathing unit for topical delivery of nitric oxide gas to a surface of the body.

16. The device of claim 10 further comprising a nitric oxide gas analyzer for measuring the concentration of nitric oxide gas flowing to the delivery interface, wherein the nitric oxide gas analyzer sends signals to the controller.

17. A device for delivery of nitric oxide gas to kill or inhibit the growth of microbes comprising:
a first source of gas;
a second source of gas;
a delivery interface adaptable for topical delivery of the gases to a mammal;

a switch valve downstream of the first and second sources of gas and upstream of the delivery interface, said switch valve for directing the flow of the gases from their sources to the delivery interface; and a controller controlling the switch valve and which commands the switch valve to switch between the first and second sources of gas on a timed basis for a number of cycles;

wherein the first source of gas has a higher concentration of nitric oxide gas than the second source of gas and the controller causes the gases to be administered according to a delivery profile that provides sufficient nitric oxide gas to affect a cumulative killing of microbes;

wherein the concentration of nitric oxide gas in the first source of gas is sufficient to overwhelm the microbes' thiol defense mechanisms and to kill or inhibit the growth of at least a portion of the microbes and the concentration of nitric oxide gas in the second source of gas is sufficient to maintain nitrosative stress on the microbes and interfere with replenishing the level of the microbes' thiol defense mechanisms; and wherein cycling between the first and second sources of gas provides a cumulative killing of the microbes.

18. The device of claim 17 wherein each cycle comprises at least first and second time periods corresponding respectively to delivery of the first and second gases.

19. The device of claim 18 wherein, in each cycle, the first time period is shorter than the second time period.

20. The device of claim 17 wherein the delivery interface comprises a bathing unit for topical delivery of the gases to a surface of the body.

21. The device of claim 17 further comprising a nitric oxide gas analyzer for measuring the concentration of nitric oxide gas flowing to the delivery interface, wherein the nitric oxide gas analyzer sends signals to the controller.

* * * * *